United States Patent
Fujita et al.

(10) Patent No.: US 11,506,789 B2
(45) Date of Patent: Nov. 22, 2022

(54) IMAGING DEVICE AND ENDOSCOPE

(71) Applicant: SONY CORPORATION, Tokyo (JP)

(72) Inventors: Goro Fujita, Kanagawa (JP); Hiroshi Yoshida, Kanagawa (JP); Kenji Tanaka, Tokyo (JP)

(73) Assignee: SONY CORPORATION, Tokyo (JP)

( * ) Notice: Subject to any disclaimer, the term of this patent is extended or adjusted under 35 U.S.C. 154(b) by 1067 days.

(21) Appl. No.: 16/095,523

(22) PCT Filed: Feb. 28, 2017

(86) PCT No.: PCT/JP2017/007854
§ 371 (c)(1),
(2) Date: Oct. 22, 2018

(87) PCT Pub. No.: WO2017/199531
PCT Pub. Date: Nov. 23, 2017

(65) Prior Publication Data
US 2019/0129037 A1 May 2, 2019

(30) Foreign Application Priority Data

May 16, 2016 (JP) .............................. JP2016-098254

(51) Int. Cl.
*A61B 1/04* (2006.01)
*G01S 17/89* (2020.01)
(Continued)

(52) U.S. Cl.
CPC ................ *G01S 17/89* (2013.01); *A61B 1/00* (2013.01); *A61B 1/00006* (2013.01);
(Continued)

(58) Field of Classification Search
CPC .......... G01S 17/89; G01S 7/481; G01S 17/86; G01S 17/88; A61B 1/00; A61B 1/00006;
(Continued)

(56) References Cited

U.S. PATENT DOCUMENTS

| 2004/0181148 A1* | 9/2004 | Uchiyama | .......... A61B 1/00183 600/173 |
| 2007/0027362 A1* | 2/2007 | Handa | .................... A61B 1/041 600/160 |
| 2020/0408598 A1* | 12/2020 | Toda | ....................... G01J 3/513 |

FOREIGN PATENT DOCUMENTS

| JP | 2014-144034 | * | 8/2014 | ............... A61B 1/00 |
| JP | 2014-144034 A | | 8/2014 | |

(Continued)

OTHER PUBLICATIONS

International Search Report dated Jun. 6, 2017 in PCT/JP2017/007854, 1 page.

(Continued)

*Primary Examiner* — Howard D Brown, Jr.
(74) *Attorney, Agent, or Firm* — Xsensus LLP

(57) ABSTRACT

[Object] To acquire distance information concerning a living tissue through an endoscope with higher accuracy irrespective of the diameter of the endoscope.
[Solution] An imaging device according to the present disclosure includes: a ranging light source section configured to output ranging light for measuring a distance at a predetermined timing; an image sensor on which an image of the imaging target is formed; a ranging light image sensor on which optical feedback of the ranging light from the imaging target is imaged; a branch optical system configured to coaxially branch incident light into three types of optical paths different from one another; and a distance information calculating section configured to calculate distance information concerning the imaging target on a basis of a result of detection of the optical feedback. In the branch optical system, a first optical path among the three types of optical paths is used as an optical path configured to guide the ranging light whose applied position on the imaging target has been controlled to the imaging target, a second optical (Continued)

path is used as an optical path configured to form an image of the imaging target on the image sensor, and a third optical path is used as an optical path configured to image the optical feedback on the ranging light image sensor. The distance information calculating section calculates a spaced distance to the imaging target by a Time Of Flight method on the basis of the result of detection of the optical feedback.

20 Claims, 13 Drawing Sheets

(51) Int. Cl.
| | |
|---|---|
| *A61B 1/00* | (2006.01) |
| *G01S 17/88* | (2006.01) |
| *G01S 7/481* | (2006.01) |
| *G01S 17/86* | (2020.01) |
| *H04N 5/369* | (2011.01) |
| *A61B 1/05* | (2006.01) |
| *A61B 1/07* | (2006.01) |
| *A61B 5/107* | (2006.01) |
| *G02B 23/24* | (2006.01) |
| *G02B 27/12* | (2006.01) |
| *G02B 27/28* | (2006.01) |

(52) U.S. Cl.
CPC ...... *A61B 1/00009* (2013.01); *A61B 1/00172* (2013.01); *A61B 1/05* (2013.01); *A61B 1/07* (2013.01); *A61B 5/1076* (2013.01); *G01S 7/481* (2013.01); *G01S 17/86* (2020.01); *G01S 17/88* (2013.01); *G02B 23/2461* (2013.01); *G02B 27/126* (2013.01); *G02B 27/283* (2013.01); *H04N 5/36965* (2018.08); *A61B 1/00167* (2013.01)

(58) Field of Classification Search
CPC ... A61B 1/00009; A61B 1/00172; A61B 1/05; A61B 1/07; A61B 5/1076; A61B 1/00167; G02B 23/2461; G02B 27/126; G02B 27/283; G02B 23/2469; G02B 23/26; H04N 5/36965
See application file for complete search history.

(56) References Cited

FOREIGN PATENT DOCUMENTS

| | | | | |
|---|---|---|---|---|
| JP | 2015-175629 A | * | 10/2015 | ............ G01S 17/87 |
| JP | 2015-175629 A | | 10/2015 | |

OTHER PUBLICATIONS

Sven Haase et al., "To F/RGB Sensor Fusion for 3-D Endoscopy", Current Medical Imaging Reviews, vol. 9, No. 2, 2013, pp. 113-119.

Jochen Penne et al., "Time-of-Flight 3-D Endoscopy", Medical Image Computing and Computer-Assisted Intervention—MICCAI 2009, vol. 5761, 8 pages.

* cited by examiner

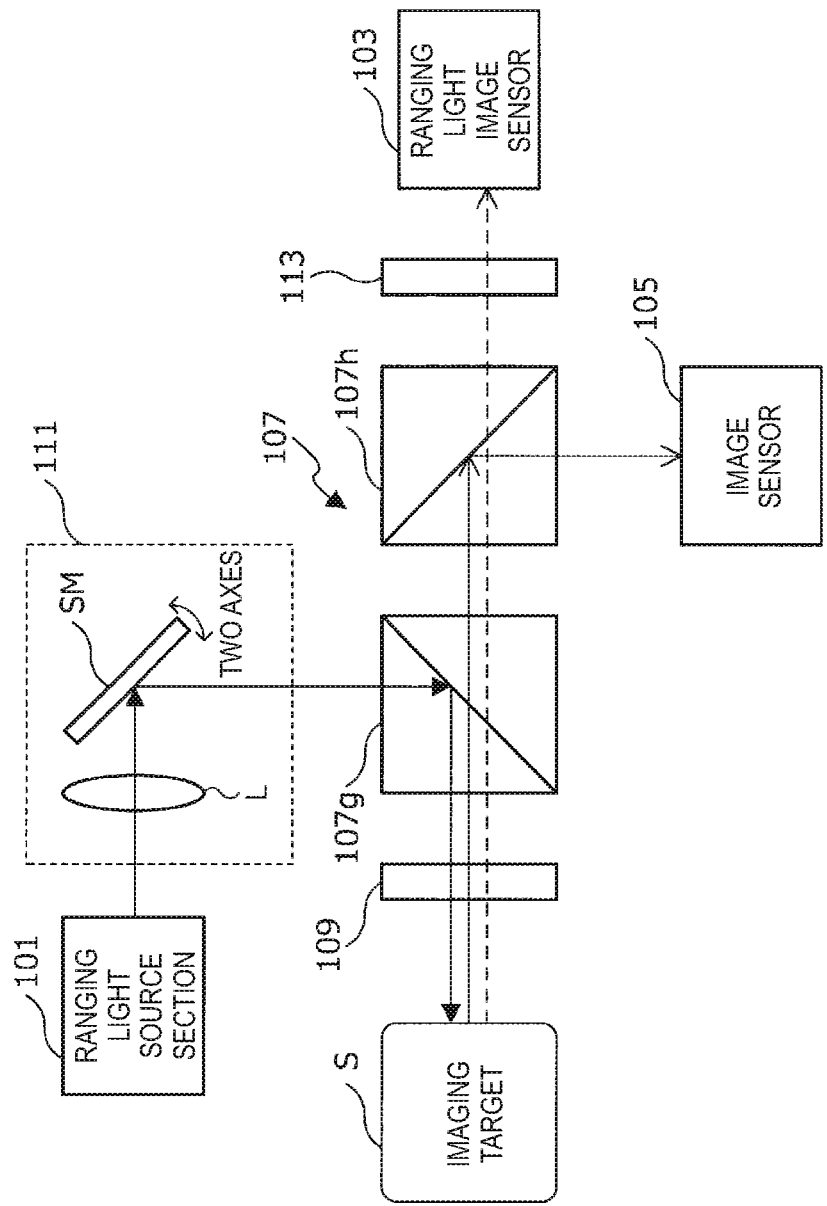

IMAGING DEVICE AND ENDOSCOPE

TECHNICAL FIELD

The present disclosure relates to an imaging device and an endoscope.

BACKGROUND ART

In recent years, surgeries are becoming less invasive, and endoscopic surgeries are being performed for intraabdominal organs, joints, and the like. Such endoscopic surgeries are advantageous in that damages to patients can be reduced, while the field of view of endoscopes is limited, and it is difficult to grasp the sense of distance. Thus, the skill of operators is required.

It is preoperatively possible to acquire three-dimensional data of a surgical site utilizing MRI, CT, or the like to push forward a surgical plan, but real-time information at a surgical stage is more useful. However, information obtained during an endoscopic surgery is limited to information that can be obtained in a limited field of view through an endoscope and that does not have a sufficient quantitative nature such as a gauge. Thus, if the size of a site or lesion which is a surgical target and the position from a landmark can be grasped quantitatively during surgery, more correct determinations and treatments can be made.

As a scale for distance measurement to be used in endoscopic surgeries, a graduated probe, bent probe, or the like is used, but is not considered as being quantitative under the present circumstances.

In recent years, as a distance measurement approach through use of an endoscope, a twin-lens stereo system through use of a parallax has been proposed, but it is difficult to apply to a less invasive small-diameter endoscope because space for installing the twin lenses is required.

Thus, a technology that enables distance measurement to be performed also with a small-diameter endoscope is demanded under the present circumstances; however, Non-Patent Literature 1 and Non-Patent Literature 2 below disclose examples of applying a single-lens Time Of Flight (TOF) system in which a parallax is not used to an endoscope.

CITATION LIST

Patent Literature

Non-Patent Literature 1: J. Penne et al., "Time-of-Flight 3-D Endoscopy", Medical Image Computing and Computer-Assisted Intervention-MICCAI 2009 Volume 5761 of the series Lecture Notes in Computer Science, p. 467-474.

Non-Patent Literature 2: S. Haase et al., "ToF/RGB Sensor Fusion for 3-D Endoscopy", Current Medical Imaging Reviews, 2013,9, p. 113-119.

DISCLOSURE OF INVENTION

Technical Problem

Non-Patent Literature 1 and Non-Patent Literature 2 above report that light for TOF was applied from an illumination port different from an observation optical path of an endoscope. Here, in Non-Patent Literature 1 above, a plastic cube placed in a pig stomach is targeted for measurement, but a measurement for a living tissue is not made, and a ranging accuracy of approximately 0.9 mm is merely obtained notwithstanding that the plastic cube having a reflection accuracy higher than a living tissue is measured. In addition, in Non-Patent Literature 2 above, though a measurement for a living tissue is made, the standard deviation is approximately 3.3 mm, which means that a ranging accuracy within 1 mm considered as being sufficient for diagnoses and studies is not obtained, and still higher accuracy is desired.

Thus, in view of the above circumstances, the present disclosure proposes an imaging device and endoscope capable of acquiring distance information concerning a living tissue through an endoscope with higher accuracy irrespective of the diameter of the endoscope.

Solution to Problem

According to the present disclosure, there is provided an imaging device including: a ranging light source section configured to output ranging light for measuring a distance to an imaging target at a predetermined timing; an image sensor on which an image of the imaging target is formed; a ranging light image sensor on which optical feedback of the ranging light from the imaging target is imaged; a branch optical system configured to coaxially branch incident light into three types of optical paths different from one another; and a distance information calculating section configured to calculate distance information concerning the imaging target on a basis of a result of detection of the optical feedback obtained by the ranging light image sensor. In the branch optical system, a first optical path among the three types of optical paths is used as an optical path configured to guide the ranging light whose applied position on the imaging target has been controlled to the imaging target, a second optical path among the three types of optical paths is used as an optical path configured to form an image of the imaging target on the image sensor, and a third optical path among the three types of optical paths is used as an optical path configured to image the optical feedback on the ranging light image sensor. The distance information calculating section calculates a spaced distance to the imaging target by a Time Of Flight method on the basis of the result of detection of the optical feedback.

In addition, according to the present disclosure, there is provided an endoscope including: an imaging device including a ranging light source section configured to output ranging light for measuring a distance to an imaging target at a predetermined timing, an image sensor on which an image of the imaging target is formed, a ranging light image sensor on which optical feedback of the ranging light from the imaging target is imaged, a branch optical system configured to coaxially branch incident light into three types of optical paths different from one another, and a distance information calculating section configured to calculate distance information concerning the imaging target on a basis of a result of detection of the optical feedback obtained by the ranging light image sensor, in which in the branch optical system, a first optical path among the three types of optical paths is used as an optical path configured to guide the ranging light whose applied position on the imaging target has been controlled to the imaging target, a second optical path among the three types of optical paths is used as an optical path configured to form an image of the imaging target on the image sensor, and a third optical path among the three types of optical paths is used as an optical path configured to image the optical feedback on the ranging light image sensor, and the distance information calculating section calculates a spaced distance to the imaging target by a Time Of Flight method on the basis of the result of detection of the optical feedback; an endoscope unit optically connected to the branch optical system; and an illumination light source section configured to output illumination light for obtaining an image of the imaging target.

According to the present disclosure, ranging light whose applied position on an imaging target has been controlled is applied to the imaging target coaxially with an optical path that forms an image from the imaging target on an image sensor through the above-described branch optical system, and optical feedback of the ranging light from the imaging target is guided to the ranging light image sensor through the branch optical system. The distance information calculating section calculates a spaced distance to the imaging target by a Time Of Flight method on the basis of a result of detection of optical feedback in the ranging light image sensor.

Advantageous Effects of Invention

According to the present disclosure as described above, it is possible to acquire distance information concerning a living tissue through an endoscope with higher accuracy irrespective of the diameter of the endoscope.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 3B is an explanatory diagram schematically showing an example of a configuration of the imaging device according to the embodiment.

MODE(S) FOR CARRYING OUT THE INVENTION

Figure 1:
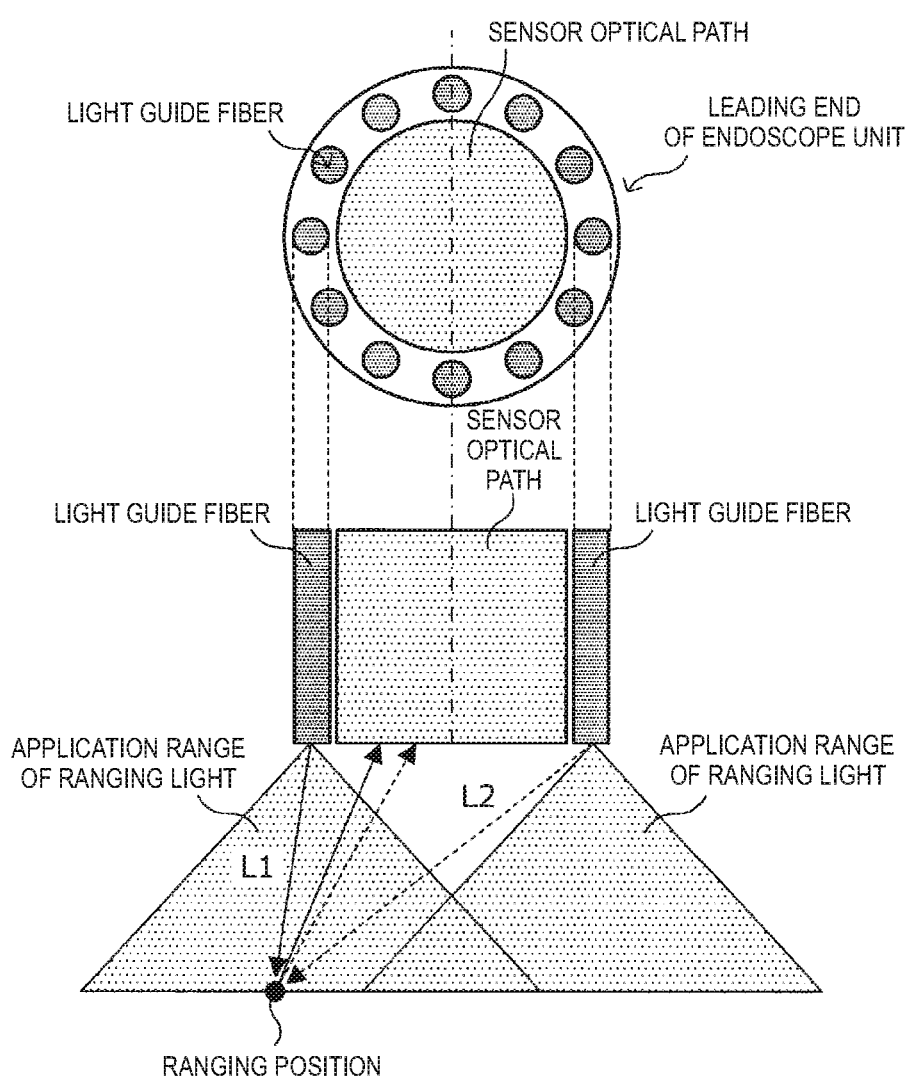
FIG. 1 is an explanatory diagram for describing a result of studies on a ranging technology through use of an endoscope.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. With regard to result of studies on ranging technology through use of endoscope
2. Embodiment
2.1. With regard to imaging device
2.2. With regard to endoscope
2.3. With regard to hardware configuration
(With Regard to Result of Studies on Ranging Technology Through Use of Endoscope)

Prior to describing an imaging device and endoscope according to an embodiment of the present disclosure, a result of studies made by the present inventors on ranging technologies disclosed in Non-Patent Literature 1 and Non-Patent Literature 2 above will be briefly described below.

The present inventors first made intense studies on the ranging technologies disclosed in Non-Patent Literature 1 and Non-Patent Literature 2 above, and considered the reason why satisfactory ranging accuracy cannot be obtained with the ranging technologies disclosed in Non-Patent Literature 1 and Non-Patent Literature 2 above. As a result, the present inventors obtained findings as will be described below. The findings the present inventors have obtained will be briefly described below with reference to FIG. 1. FIG. 1 is an explanatory diagram for describing the result of studies on a ranging technology through use of an endoscope.

In the case of applying a ranging technology through use of the Time Of Flight (TOF) method to an endoscope, it is necessary to install, in the endoscope, a light source section that outputs ranging light having a predetermined wavelength to be utilized in the TOF method and a ranging light detecting section for detecting optical feedback of such ranging light from a target of measurement.

Here, in Non-Patent Literature 1 and Non-Patent Literature 2 above, ranging light is guided to the surface of the target of measurement by connecting the ranging light output from the light source section to light guide fibers provided in an endoscope unit. Here, the light guide fibers are provided in an endoscope unit in order to emit illumination light such as white light, for example, to a target of observation of the endoscope. Thus, if the ranging light is connected to such light guide fibers, the ranging light will be applied to the surface of the target of measurement with a certain extent as schematically shown in FIG. 1.

In the case where the ranging light is applied with a certain extent as schematically shown in FIG. 1, the ranging light is also applied to a wide area other than a ranging position, and thus, the amount of light applied to a desired ranging position is reduced. As a result, utilization efficiency of the ranging light is reduced, so that it is expected that the signal-to-noise ratio of optical feedback detected by the ranging light detecting section is reduced. As a result, it is considered that satisfactory ranging accuracy is not obtained in Non-Patent Literature 1 and Non-Patent Literature 2 above.

In addition, the leading end of the endoscope unit often has a structure in which light guide fibers for guiding illumination light are provided around a sensor optical path for guiding an image (for example, a visible light image) of a target of observation to an imaging unit, as schematically shown at the upper part of FIG. 1. In this case, an optical path length (for example, an optical path length L1 in FIG. 1) of ranging light that is applied from a certain light guide fiber to the ranging position and then returns to the ranging light detecting section and an optical path length (for example, an optical path length L2 in FIG. 1) of ranging light that is applied from another light guide fiber to the ranging position and then returns to the ranging light detecting section do not agree in many cases. For this reason, an optical path difference occurs in detected ranging light, which contributes to a steady state error. As a result, in Non-Patent Literature 2 above, it is considered that satisfactory ranging accuracy is not obtained also due to such an optical path difference.

Note that, since the ranging light is guided using a single optical fiber in Non-Patent Literature 1 above, it is considered that a difference between light guide fibers as described above does not occur; however, since an optical fiber having a large diameter whose fiber diameter is 200 μm is used in Non-Patent Literature 1 above, it is supposed that an optical path difference similar to the foregoing occurs.

From the result of studies as described above, the present inventors have reached the conclusion that, in the case of connecting ranging light for TOF to light guide fibers of the endoscope unit, it is difficult to obtain more excellent ranging accuracy. As a result of further studies with such a conclusion, the present inventors have obtained findings that, by making an optical path for guiding ranging light to the surface of a target of measurement and an optical path (also serving as an optical path for guiding optical feedback of ranging light from the target of measurement to the ranging light detecting section) for guiding an image of a target of observation to the imaging unit coaxial, the light source of ranging light and the ranging position have a conjugate relation because of the structure of the endoscope, which can prevent an optical path difference as described above from occurring, and can further improve the ranging accuracy.

In addition, by making an optical path for guiding ranging light to the surface of the target of measurement and an optical path for guiding an image of a target of observation to the imaging unit coaxial, it is possible to narrow an application range of ranging light. Thus, findings that it is not only possible to improve utilization efficiency of ranging light, but also it is possible to apply ranging light to a desired position with high accuracy by controlling the applied position of ranging light could also be obtained.

As a result of further studies made on the basis of such findings, the present inventors have completed an imaging device and endoscope according to the present disclosure as described below in detail.

(Embodiment)
<With Regard to Imaging Device>

The imaging device according to an embodiment of the present disclosure will be described below in detail with reference to FIG. 2 to FIG. 11.

Figure 2:
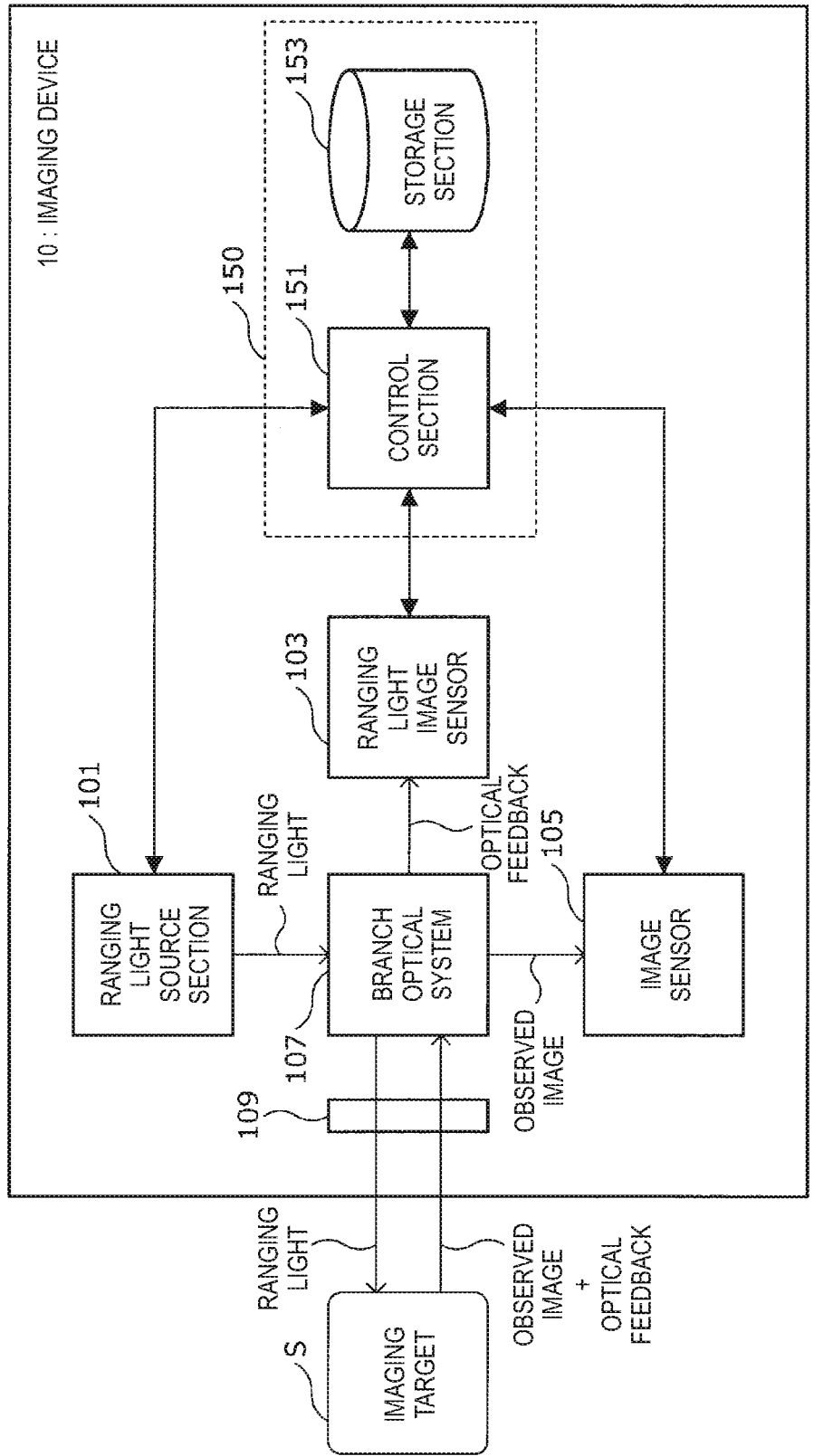
FIG. 2 is a block diagram schematically showing an overall configuration of an imaging device according to an embodiment of the present disclosure.
Figure 3A:
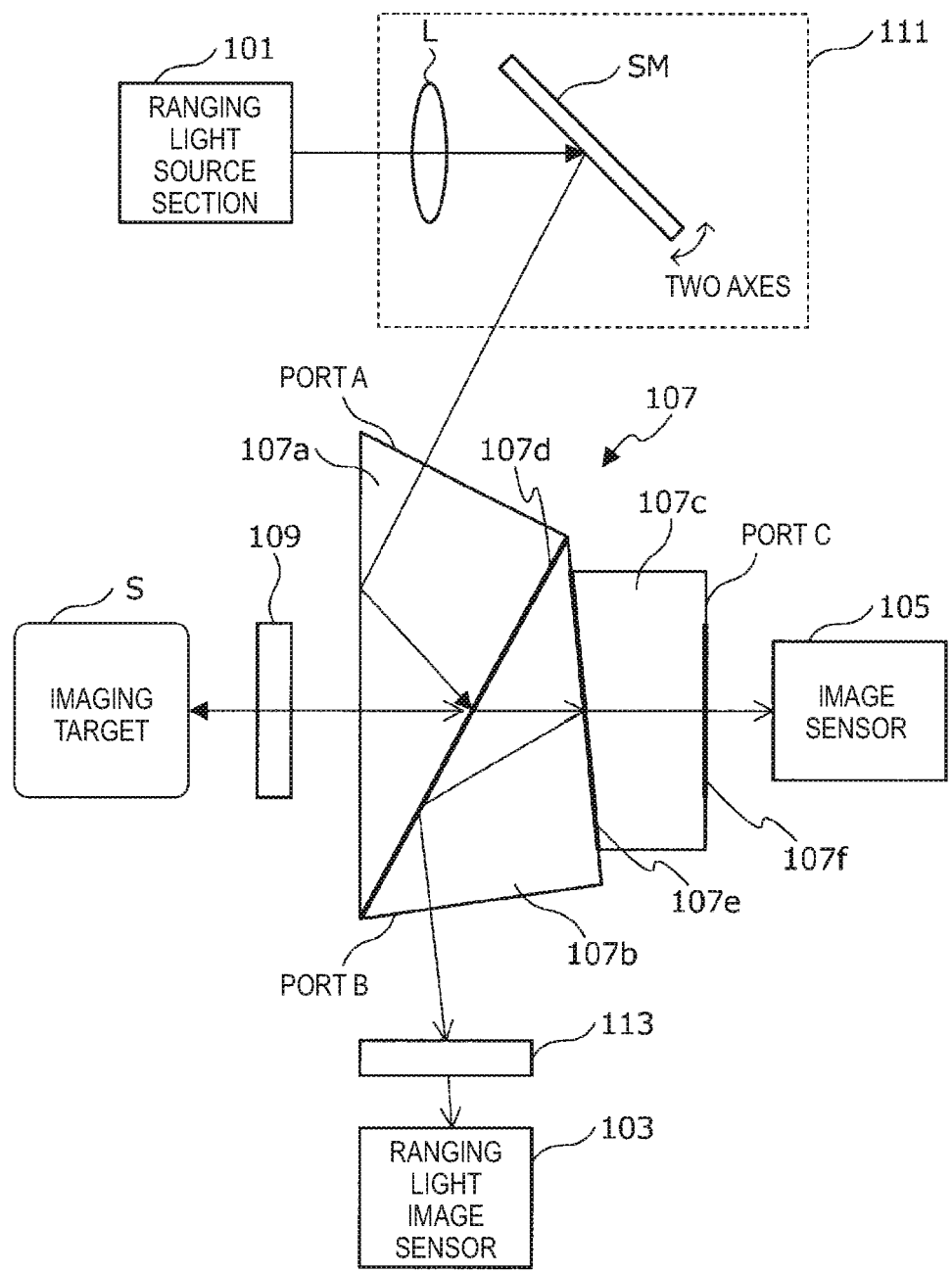
FIG. 3A is an explanatory diagram schematically showing an example of a configuration of the imaging device according to the embodiment.
Figure 4:
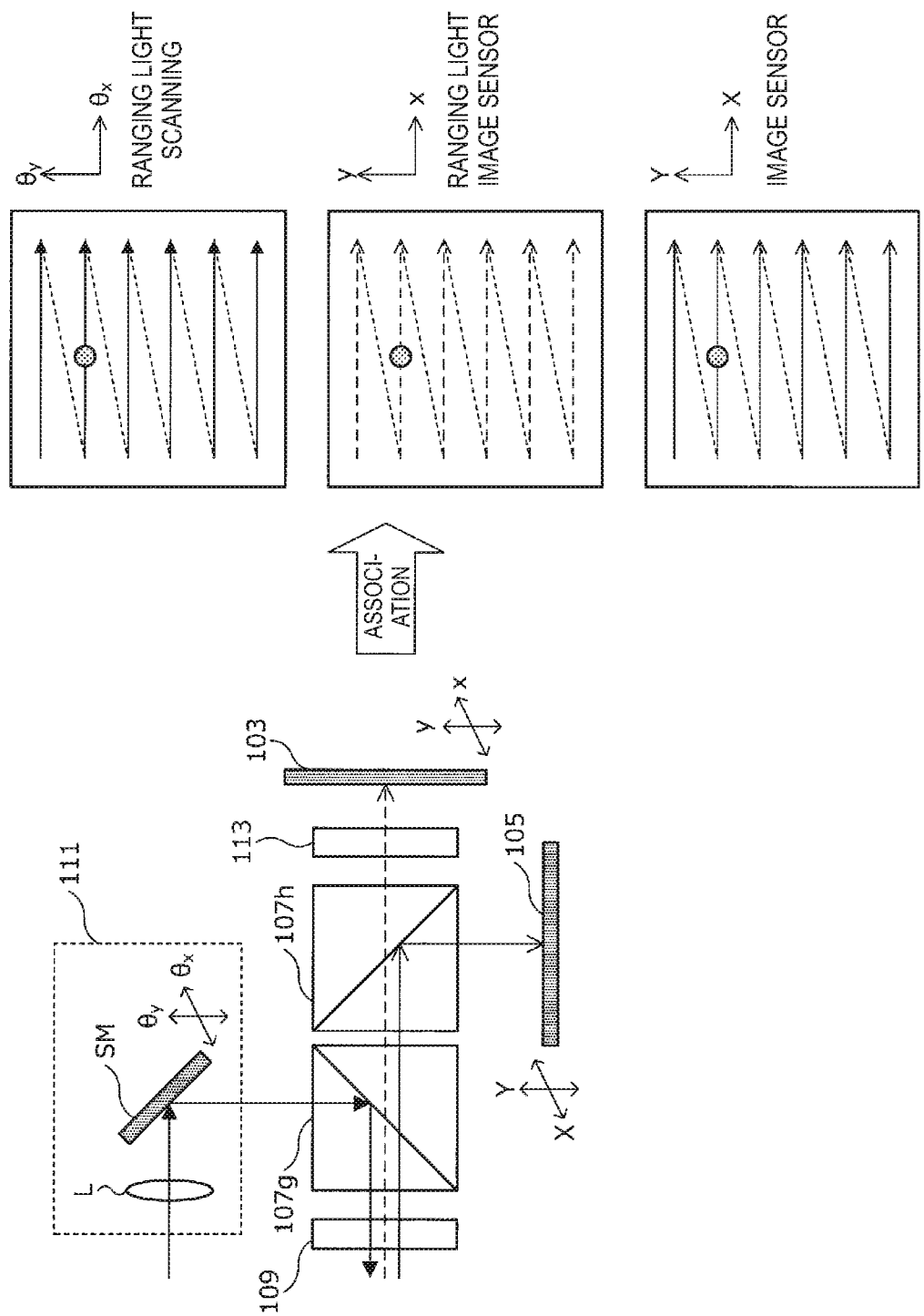
FIG. 4 is an explanatory diagram for describing the imaging device according to the embodiment.
Figure 5:
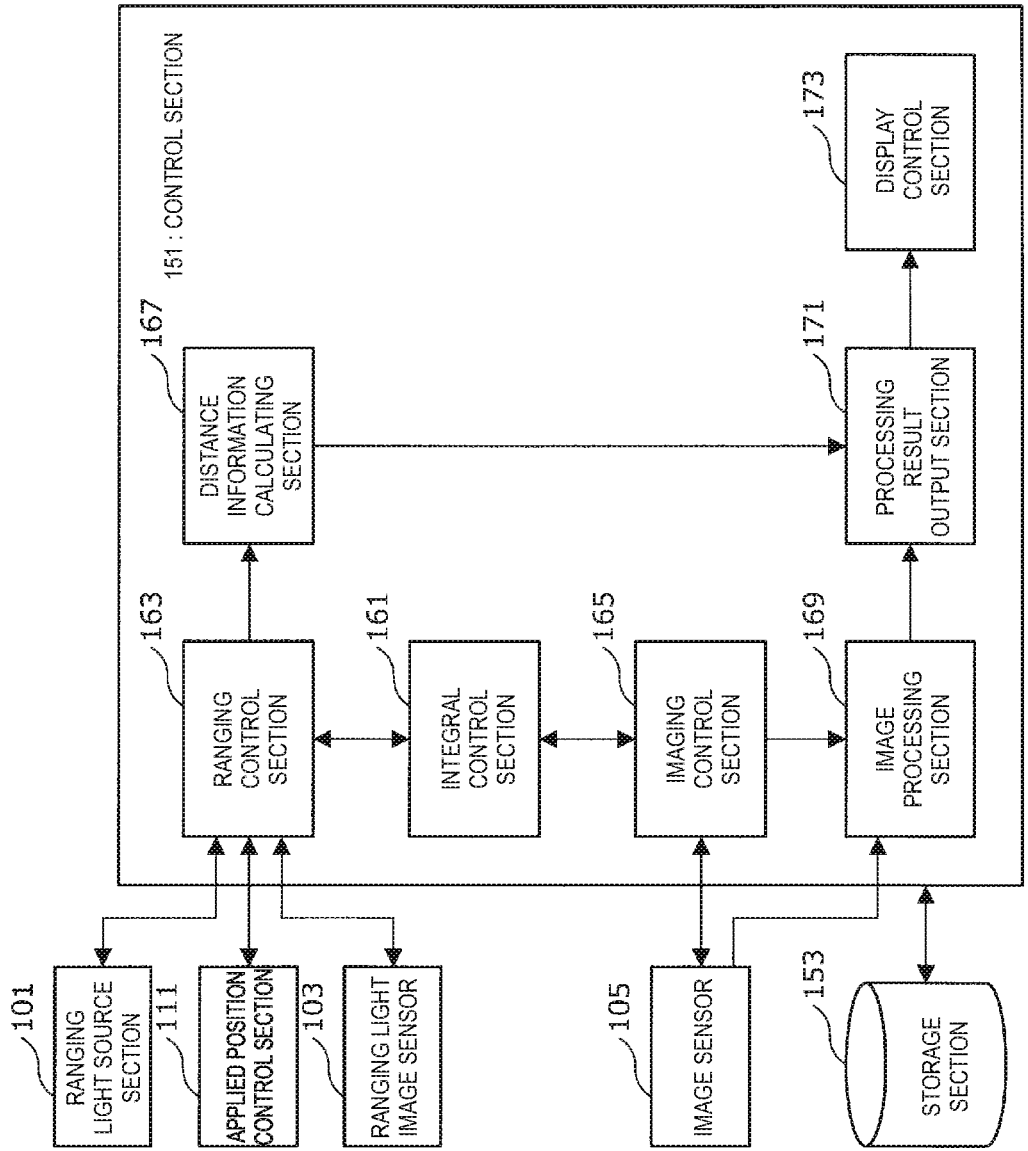
FIG. 5 is a block diagram showing an example of a configuration of an arithmetic processing section that the imaging device according to the embodiment has.

FIG. 2 is a block diagram schematically showing an overall configuration of the imaging device according to the present embodiment, and FIG. 3A and FIG. 3B are explanatory diagrams schematically showing an example of a configuration of the imaging device according to the present embodiment. FIG. 4 is an explanatory diagram for describing the imaging device according to the present embodiment, and FIG. 5 is a block diagram showing an example of a configuration of an arithmetic processing section that the imaging device according to the present embodiment has. FIG. 6 to FIG. 10 are diagrams for describing control processing in the imaging device according to the present embodiment, and FIG. 11 is an explanatory diagram schematically showing an example of a configuration of the imaging device according to the present embodiment.

[With Regard to Overall Configuration of Imaging Device]

The imaging device according to the present embodiment is a device that images an imaging target (for example, various living tissues, or the like) to generate an observed image of the imaging target and measures the distance to the imaging target by the TOF method. In addition, the imaging device according to the present embodiment can be optically connected to a publicly-known endoscope unit (for example, a publicly-known medical endoscope and a joint mirror, an industrial endoscope, or the like) to carry out processing of generating an observed image of the imaging target and ranging processing as described above through such an endoscope unit.

Such an imaging device has an imaging optical system that generates an observed image of the imaging target while detecting a signal related to the distance to the imaging target and an arithmetic processing section that controls the imaging optical system and generates distance information concerning the imaging target utilizing a result of detection of the signal related to the distance to the imaging target obtained in such an imaging optical system.

Specifically, as shown in FIG. 2, an imaging optical system of an imaging device 10 at least has a ranging light source section 101, a ranging light image sensor 103, an image sensor 105, and a branch optical system 107. In addition, it is preferable that such an imaging optical system further has a quarter wave plate 109 as an optical element.

In addition, an arithmetic processing section 150 of the imaging device 10 at least has a control section 151 and a storage section 153, as shown in FIG. 2.

The ranging light source section 101 is a light source that outputs ranging light for measuring the distance to an imaging target S at a predetermined timing under the control exerted by the arithmetic processing section 150 which will be described later. Here, as the ranging light source section 101, it is possible to utilize a publicly-known light source such as various solid state lasers, semiconductor lasers, superluminescent diodes, light emitting diodes, or the like, for example. In addition, ranging light output from the ranging light source section 101 is not particularly limited as long as it is light that can be utilized for the TOF method, but may be pulsed light intermittently oscillated with a predetermined pulse width, or may be polarized light having predetermined polarization.

The wavelength of ranging light output from the ranging light source section 101 is not particularly limited, but preferably has a wavelength as distant as possible from the wavelength band of an observed image of the imaging target S captured by the image sensor 105 which will be described later. For example, in the case where an observed image of the imaging target S in the visible light band is captured by the image sensor 105 which will be described later, it is preferable that the wavelength of ranging light is a wavelength (for example, blue light having a wavelength of 405 nm or near-infrared light having a wavelength of approximately 820 nm) close to the both ends of the visible light band (for example, a wavelength of approximately 400 to 800 nm). Accordingly, it is possible to suppress excessive superimposition of an image of ranging light on an observed image of the imaging target S generated in the image sensor 105.

The ranging light output from the ranging light source section 101 is guided to the branch optical system 107 which will be described later after the applied position (in other words, the ranging position by the TOF method) on the surface of the imaging target S is controlled.

The ranging light image sensor 103 is an image sensor on which optical feedback of ranging light from the imaging target S is imaged, and captures the above-described image of optical feedback at a predetermined timing under the control exerted by the arithmetic processing section 150 which will be described later. Such a ranging light image sensor 103 is not particularly limited as long as it is an image sensor that can be applied to the TOF method, but a publicly-known image sensor called a so-called TOF sensor can be applied. Note that it is more preferable that such a ranging light image sensor 103 is an image sensor having a global shutter.

A result of detection of optical feedback of ranging light obtained by the ranging light image sensor 103 is output to the arithmetic processing section 150 which will be described later to be utilized for generation of distance information concerning the imaging target S.

An observed image of the imaging target S is formed on the image sensor 105. Such an image sensor 105 captures the above-described observed image at a predetermined timing under the control exerted by the arithmetic processing section 150 which will be described later to generate an observed image of the imaging target S. Such an image sensor 105 is not particularly limited, but an appropriate image sensor may be selected in accordance with images in various wavelength bands desired to be acquired for the imaging target S. For example, in the case where an observed image of the imaging target S in the visible light band is desired to be acquired by the image sensor 105, it is possible to utilize a publicly-known image sensor such as various charge-coupled device (CCD) image sensors, or complementary MOS (CMOS) image sensors, for example. In addition, in the case where an observed image of the imaging target S in the near-infrared light band is desired to be acquired by the image sensor 105, a publicly-known image sensor having sensitivity to the near-infrared light band may be utilized. Note that it is more preferable that such an image sensor 105 is an image sensor having a global shutter.

The branch optical system 107 is an optical system that branches incident light coaxially into three types of optical paths different from one another. As schematically shown in FIG. 2, only a single optical path exists on the imaging target S side of the branch optical system 107 according to the present embodiment, while three types of optical paths, an optical path leading to the ranging light source section 101, an optical path leading to the ranging light image sensor 103, and an optical path leading to the image sensor 105, exist on the other end of the optical path of the branch optical system 107. That is, in such a branch optical system 107, a first optical path among the three types of optical paths as described above is used as an optical path for guiding ranging light whose applied position on the imaging target S has been controlled to the imaging target S, a second optical path among the three types of optical paths is used as an optical path for forming an image of the imaging target S on the image sensor 105, and a third optical path among the three types of optical paths is used as an optical path for imaging optical feedback on the ranging light image sensor 103.

A specific example of such a branch optical system 107 will be described below in detail again.

It is preferable that the quarter wave plate 109 is provided on an optical axis between the branch optical system 107 and the imaging target S in order to control the polarization direction of ranging light. By controlling the polarization direction of ranging light by the quarter wave plate 109, it is possible to further efficiently branch ranging light before being applied to the imaging target S and optical feedback of ranging light from the imaging target S in the branch optical system 107. Such a quarter wave plate 109 is not particularly limited, but it is possible to utilize a publicly-known quarter wave plate.

In addition, various optical elements such as various lenses may be provided on the optical axis between the branch optical system 107 according to the present embodiment and the imaging target S, in addition to the quarter wave plate 109 as described above.

The arithmetic processing section 150 is a processing section that controls the imaging optical system as described above, and generates distance information concerning the imaging target S utilizing a result of detection of a signal (that is, optical feedback of ranging light) related to the distance to the imaging target S obtained in such an imaging optical system. This arithmetic processing section 150 at least has the control section 151 and the storage section 153 as schematically shown in FIG. 2.

The control section 151 is implemented by a central processing unit (CPU), read only memory (ROM), random access memory (RAM), or the like, for example. The control section 151 is a processing section that generally controls the operation of the imaging device 10 according to the present embodiment, and is also capable of generating various types of secondary information on the basis of various signals output from the imaging optical system. In the imaging device 10 according to the present embodiment, when such a control section 151 functions appropriately, an observed image of the imaging target S is generated, and various types of distance information concerning the imaging target S are generated.

A detailed configuration of such a control section 151 will be described below again.

The storage section 153 is an example of a storage device that the arithmetic processing section 150 includes. In the storage section 153, various parameters, progress of processing, and the like needed to be stored when the arithmetic processing section 150 according to the present embodiment performs some processing, or various databases, programs, and the like are recorded as appropriate. The control section 151 can freely carry out processing of reading/writing from/in this storage section 153.

[Specific Example of Imaging Optical System]

Next, a specific example of the imaging optical system according to the present embodiment will be described with reference to FIG. 3A to FIG. 4. Note that the specific example of the imaging optical system which will be described below is merely an example, and the imaging optical system according to the present embodiment is not limited to the following specific example.

FIG. 3A schematically shows an imaging optical system in the case where ranging light of a point light source output from the ranging light source section 101 is guided to the branch optical system 107 including a spectrum prism having three types of optical prisms bonded to one another after the applied position is controlled by an applied position control section 111 that controls the applied position of such ranging light on the imaging target S.

In the example shown in FIG. 3A, ranging light emitted from the ranging light source section 101, for example, having a predetermined polarization direction and having a wavelength of 405 nm or 820 nm, for example, is guided to a scanning mirror SM through a lens L provided as the applied position control section 111. The scanning mirror SM is a mirror that is movable in two-axis directions which are the direction of the sheet of drawing of FIG. 3A and the direction orthogonal to the sheet of drawing, and when such a scanning mirror SM is controlled appropriately by the arithmetic processing section 150, the applied position (that is, ranging position) of ranging light can be controlled. The ranging light whose applied position has been controlled by the scanning mirror SM is guided to the branch optical system 107 including a spectrum prism having three types of optical prisms bonded to one another.

In the branch optical system 107 shown in FIG. 3A, a first prism 107a, a second prism 107b, and a third prism 107c are arranged in the order closer to the imaging target S, and these three types of optical prisms are bonded to one another.

In the branch optical system 107 as shown in FIG. 3A, there is a single optical path at the end on the imaging target S side, while the optical path is branched into three types at the other end of the branch optical system 107. Hereinafter, the end of the optical path after branching in the first prism 107a will be referred to as a port A, and similarly, the end of the optical path after branching in the second prism 107b will be referred to as a port B, and the end of the optical path after branching in the third prism 107c will be referred to as a port C.

Conventionally, such a branch optical system is used for coaxially branching light incident from the side of an imaging target into three optical paths or multiplexing light incident from the respective ports for application to the imaging target. That is, conventionally, in such a branch optical system, the traveling direction of light that propagates within the branch optical system is merely one direction, such as the direction from the left to the right in FIG. 3A or the direction from the right to the left.

However, in the branch optical system 107 according to the present embodiment, at least part of the optical paths among the three types of optical paths is utilized as an optical path for guiding ranging light to the imaging target S, and the other two optical paths are utilized as optical paths for imaging light guided from the imaging target S on the respective image sensors.

In order to achieve bidirectional light propagation within the branch optical system 107 as described above, the branch optical system 107 according to the present embodiment causes a bonding surface 107d between the first prism 107a and the second prism 107b and a bonding surface 107e between the second prism 107b and the third prism 107c to function as at least any of a beam splitter (BS), a polarizing beam splitter (PBS), and a wavelength selection filter. Accordingly, it is possible to distinguish rays of light that propagate through the three types of optical paths from one another. In addition, it is also possible to cause an output end surface 107f of the third prism 107c to function as at least either a polarizing beam splitter or a wavelength selection filter.

As schematically shown in FIG. 3A, there are positions at which the three types of optical equipment, the port A to the port C or the like, can be installed in the branch optical system 107, whilst in the imaging device 10 according to the present embodiment, the ranging light source section 101 is connected to any of the port A to the port C, and the ranging light image sensor 103 and the image sensor 105 are provided for the remaining ports. In the example shown in FIG. 3A, the ranging light source section 101 is connected to the port A of the branch optical system 107, the ranging light image sensor 103 is provided for the port B of the branch optical system 107, and the image sensor 105 is provided for the port C of the branch optical system 107.

Note that what is arranged at which port of the branch optical system 107 is not limited to the example shown in FIG. 3A, but it is possible to install the ranging light source section 101, the ranging light image sensor 103, and the image sensor 105 at any port positions of the branch optical system 107.

The branch optical system 107 shown in FIG. 3A causes the bonding surface 107d to function as a polarizing beam splitter (PBS) to reflect ranging light from the ranging light source section 101 with a high reflectivity, and to pass optical feedback of ranging light guided from the imaging target S and an observed image of the imaging target S with a high transmittance. As a result, ranging light from the ranging light source section 101 is reflected by the bonding surface 107d, and the polarization direction is changed at the quarter wave plate 109, and then guided to the imaging target S to be applied to an appropriate applied position.

In addition, illumination light of white light, for example, is applied to the imaging target S from an illumination light source section (not shown) provided external to the imaging device 10 according to the present embodiment. An observed image of the imaging target S obtained by such illumination light and optical feedback of applied ranging light pass through the quarter wave plate 109 again, and then enter the branch optical system 107. The observed image of the imaging target S and the optical feedback of ranging light pass through the bonding surface 107d to reach the bonding surface 107e of the branch optical system 107.

The bonding surface 107e functions as a wavelength selection filter that reflects the wavelength of ranging light and passes light of the other wavelengths. Accordingly, the optical feedback of ranging light is reflected by the bonding surface 107e to be guided to the ranging light image sensor 103, and the observed image of the imaging target S passes through the bonding surface 107e to be guided to the image sensor 105.

Here, even in the case of providing a wavelength selection filter at the bonding surface 107e, part of the optical feedback of ranging light passes through the wavelength selection filter to become leak light and to be imaged on the image sensor 105. In the imaging device 10 according to the present embodiment, such leak light of ranging light is utilized actively, and is utilized as a guide indicating a ranging position. This allows a user of the imaging device 10 according to the present embodiment to easily grasp a position (that is, the ranging position) to which the ranging light is applied.

Note that it is also possible to intentionally control the reflectivity of ranging light in the wavelength selection filter provided at the bonding surface 107e to set such that part of the optical feedback of ranging light is imaged on the image sensor 105 to more actively utilize the leak light of ranging light as a guide indicating the ranging position.

Note that, as shown in FIG. 3A, the optical feedback of ranging light reflected by the bonding surface 107e is guided to the ranging light image sensor 103 provided at the port B, whilst it is preferable to further provide a bandpass filter 113 that only passes light corresponding to the wavelength of ranging light on the optical axis between the branch optical system 107 and the ranging light image sensor 103, as shown in FIG. 3A. Accordingly, it is possible to prevent light other than the optical feedback of ranging light from being imaged on the ranging light image sensor 103, and it is possible to further improve the ranging accuracy.

In the imaging optical system shown in FIG. 3A, the optical feedback of ranging light having reached the ranging light image sensor 103 is detected by the ranging light image sensor 103, and a detection result is output to the arithmetic processing section 150. In addition, the observed image of the imaging target S having reached the image sensor 105 is captured by the image sensor 105, and the generated observed image of the imaging target S is output to the arithmetic processing section 150.

Here, the case of using a spectrum prism having three types of optical prisms bonded to one another as the branch optical system 107 is illustrated in the example shown in FIG. 3A, whilst it is also possible to adopt an optical system including a polarizing beam splitter and a beam splitter as shown in FIG. 3B as the branch optical system 107 according to the present embodiment.

In the example shown in FIG. 3B, ranging light output from the ranging light source section 101 is reflected by a polarizing beam splitter 107g positioned on the imaging target S side to be applied to the imaging target S, while optical feedback of ranging light from the imaging target S and an observed image of the imaging target S pass through the polarizing beam splitter 107g to be guided to a beam splitter 107h. In the beam splitter 107h, the observed image of the imaging target S is reflected by a reflective surface to be guided to the image sensor 105, and the optical feedback of ranging light passes through the reflective surface to be guided to the ranging light image sensor 103.

Also in the example shown in FIG. 3B, leak light of ranging light imaged on the image sensor 105 is utilized as a guide indicating the ranging position. In addition, it is preferable to further provide the bandpass filter 113 that only passes light corresponding to the wavelength of ranging light similarly to FIG. 3A on an optical axis between the beam splitter 107h and the ranging light image sensor 103.

In the imaging device 10 according to the present embodiment, the applied position of ranging light is scanned in accordance with the direction that the scanning mirror SM faces (for example, a combination ($\theta_x$, $\theta_y$) of angles of the scanning mirror SM), as schematically shown in FIG. 4. In addition, in the imaging device 10 according to the present embodiment, the optical feedback of ranging light is imaged at a certain position (x, y) of the ranging light image sensor 103, and the leak light of ranging light is imaged at a certain position (X, Y) of the image sensor 105.

On this occasion, it is preferable that the ranging light image sensor 103 and the image sensor 105 are installed in the branch optical system 107 such that pixel arrangements correspond to each other, and adjustment is made such that the direction of applying ranging light, the position at which the optical feedback of ranging light is imaged, and the position at which the leak light of ranging light is imaged agree. Accordingly, it is possible to further improve the ranging accuracy of the imaging device 10 according to the present embodiment.

The imaging optical system according to the present embodiment has been described above in detail with reference to FIG. 3A to FIG. 4.

[With Regard to Configuration of Control Section 151]

Next, with reference to FIG. 5 to FIG. 10, a detailed configuration of the control section 151 according to the present embodiment will be described, and control processing carried out in the imaging device 10 according to the present embodiment will be described in detail.

The control section 151 that the arithmetic processing section 150 according to the present embodiment has at least has an integral control section 161, a ranging control section 163, an imaging control section 165, a distance information calculating section 167, an image processing section 169, a processing result output section 171, and a display control section 173, as schematically shown in FIG. 5.

The integral control section 161 is implemented by a CPU, a ROM, a RAM, an input device, an output device, a communication device, or the like, for example. The integral control section 161 is a processing section that integrally controls various operations and functions achieved in the imaging device 10 according to the present embodiment. When various user operations are input to the imaging device 10 according to the present embodiment, a control signal is output to a processing section corresponding to an input user operation so as to achieve a function corresponding to the input user operation. When such an integral control section 161 runs appropriately, respective processing sections that the control section 151 has can cooperate with one another to achieve various functions. In addition, such an integral control section 161 also functions as a processing section that achieves various functions other than the ranging function and the observed image generating function achieved in the imaging device 10 according to the present embodiment.

The ranging control section 163 is implemented by a CPU, ROM, RAM, communication device, or the like, for example. The ranging control section 163 controls the applied position control section 111 and the ranging light image sensor 103 to be brought into a desired state by outputting predetermined control signals to the ranging light source section 101, the applied position control section 111, and the ranging light image sensor 103 provided in the imaging optical system, respectively.

In more detail, the ranging control section 163 outputs a predetermined control signal to the applied position control section 111 to cause the scanning mirror MS to perform scanning. In addition, in accordance with a user operation input to the arithmetic processing section 150 (in more detail, the integral control section 161) by various methods, the ranging control section 163 outputs, to the ranging light source section 101, a control signal that causes ranging light to be output at a predetermined intensity at a timing when the scanning mirror MS reaches a position corresponding to a user desired ranging position, and outputs a control signal that controls the imaging timing of the ranging light image sensor 103. On this occasion, the ranging control section 163 synchronizes the imaging timing of optical feedback of ranging light in the ranging light image sensor 103 and the imaging timing of the observed image of the imaging target S in the image sensor 105 to a desired timing, while cooperating with the imaging control section 165 which will be described later with each other through the integral control section 161.

In addition, when acquiring a signal concerning a result of detection of the optical feedback of ranging light from the ranging light image sensor 103, the ranging control section 163 outputs the obtained signal to the distance information calculating section 167 which will be described later. Accordingly, distance information calculating processing based on the acquired detection signal will be carried out by the distance information calculating section 167 which will be described later.

The imaging control section 165 is implemented by a CPU, ROM, RAM, communication device, or the like for example. The imaging control section 165 controls the image sensor 105 to be brought into a desired state by outputting a predetermined control signal to the image sensor 105.

In more detail, the imaging control section 165 causes an observed image of the imaging target S formed on the image sensor 105 to be captured at a predetermined timing to generate the observed image of the imaging target S, while cooperating with the ranging control section 163 with each other through the integral control section 161. The observed image generated in the image sensor 105 is output to the image processing section 169 which will be described later, and is subjected to various types of image processing by the image processing section 169 according to necessity.

In addition, in the case where the imaging device 10 according to the present embodiment is mounted on an endoscope unit having an illumination light source section that outputs predetermined illumination light, the imaging control section 165 controls the illumination light source section provided in the endoscope unit to apply or turn off illumination light at a desired timing.

Note that control processing carried out by the imaging device 10 according to the present embodiment when the ranging control section 163 and the imaging control section 165 cooperate with each other will be described below in detail again.

The distance information calculating section 167 is implemented by a CPU, ROM, RAM, or the like, for example. The distance information calculating section 167 calculates distance information concerning the imaging target S on the basis of a result of detection of optical feedback of ranging light obtained by the ranging light image sensor 103 provided in the imaging optical system.

In more detail, the distance information calculating section 167 first calculates a spaced distance between the imaging target S and the ranging light image sensor 103 or a spaced distance between an object having an optically conjugate positional relation with the ranging light image sensor 103 and the imaging target S, on the basis of a result of detection of optical feedback of ranging light obtained by the ranging light image sensor 103.

Note that, as to the object having an optically conjugate positional relation with the ranging light image sensor 103, in the case where the imaging device 10 according to the present embodiment is mounted on publicly-known various endoscopes (for example, a general medical endoscope and joint mirror, an industrial endoscope, and the like), for example, an objective lens provided at the leading end of the endoscope has an optically conjugate positional relation with the ranging light image sensor 103 and the image sensor 105 because of the structural characteristics of the endoscope. In this case, the spaced distance calculated by the distance information calculating section 167 becomes equivalent to a spaced distance between the objective lens and the imaging target S.

Here, in the TOF method to which attention is paid in the present embodiment, the distance that light travels for a time required from application of ranging light from the ranging light source section 101 to detection of optical feedback of ranging light in the ranging light image sensor 103 becomes equal to twice the spaced distance of interest. Therefore, the distance information calculating section 167 calculates the spaced distance to the imaging target S on the basis of the time required from application of ranging light from the ranging light source section 101 to detection of optical feedback of ranging light in the ranging light image sensor 103 or a phase difference between the time when the ranging light is applied and the time when the optical feedback of ranging light is detected.

In addition, the distance information calculating section 167 is capable of further calculating distance information concerning position coordinates of the applied position (that is, ranging position) of ranging light on the basis of angular information (that is, information concerning the applied position of ranging light) of the scanning mirror SM in the applied position control section 111 and the calculated spaced distance to the imaging target S.

Further, in the case where optical feedback is detected at a plurality of positions during an exposure time of the ranging light image sensor 103, the distance information calculating section 167 is capable of calculating position coordinates of the ranging position for each of the positions at which optical feedback has been detected, and calculating a relative distance between the respective ranging positions.

Note that distance information calculating processing as described above will be described below again.

Upon calculating various types of distance information concerning the imaging target S as described above, the distance information calculating section 167 outputs the calculated distance information to the processing result output section 171 which will be described later.

The image processing section 169 is implemented by a CPU, ROM, RAM, or the like, for example. The image processing section 169 is a processing section that carries out predetermined image processing for image data of a captured image (observed image) generated in the image sensor 105 in the imaging optical system. Image processing carried out in such an image processing section 169 is not particularly limited, but it is possible to carry out publicly-known various types of image processing.

Upon carrying out various types of image processing for the observed image generated in the image sensor 105, the image processing section 169 outputs various images after the processing to the processing result output section 171 and the like.

The processing result output section 171 is implemented by a CPU, a ROM, a RAM, an output device, a communication device, or the like, for example. The processing result output section 171 outputs various captured images captured in the imaging device 10 according to the present embodiment, various types of distance information calculated by the distance information calculating section 167, results of various types of image processing carried out by the image processing section 169, or the like to a user. For example, the processing result output section 171 is capable of outputting information concerning these results to the display control section 173. Accordingly, information concerning these results will be output to a display section (not shown) included in the imaging device 10 or a display section (for example, an external monitor, or the like) provided external to the imaging device 10. In addition, the processing result output section 171 is capable of outputting information concerning obtained results as a printed matter, or to an external information processing device, a server, or the like as data.

The display control section 173 is implemented by a CPU, a ROM, a RAM, an output device, a communication device, or the like, for example. The display control section 173 performs display control when displaying various results output from the processing result output section 171 on an output device such as a display included in the imaging device 10, an output device provided external to the imaging device 10, or the like. This allows the user of the imaging device 10 to grasp the various results in situ.

With Regard to Control Processing of Imaging Optical System

Next, with reference to FIG. 6 to FIG. 10, control processing of the imaging optical system carried out in the control section 151 according to the present embodiment will be described in detail while providing examples.

Hereinafter, with regard to imaging optical systems as shown in FIG. 3A and FIG. 3B, control processing will be described providing, as an example, the case in which the ranging light image sensor 103 having a global shutter and the image sensor 105 perform output in an interline-type frame-transfer system. Note that it is assumed that the ranging light image sensor 103 and the image sensor 105 have a pixel size of m×n pixels.

Figure 6:
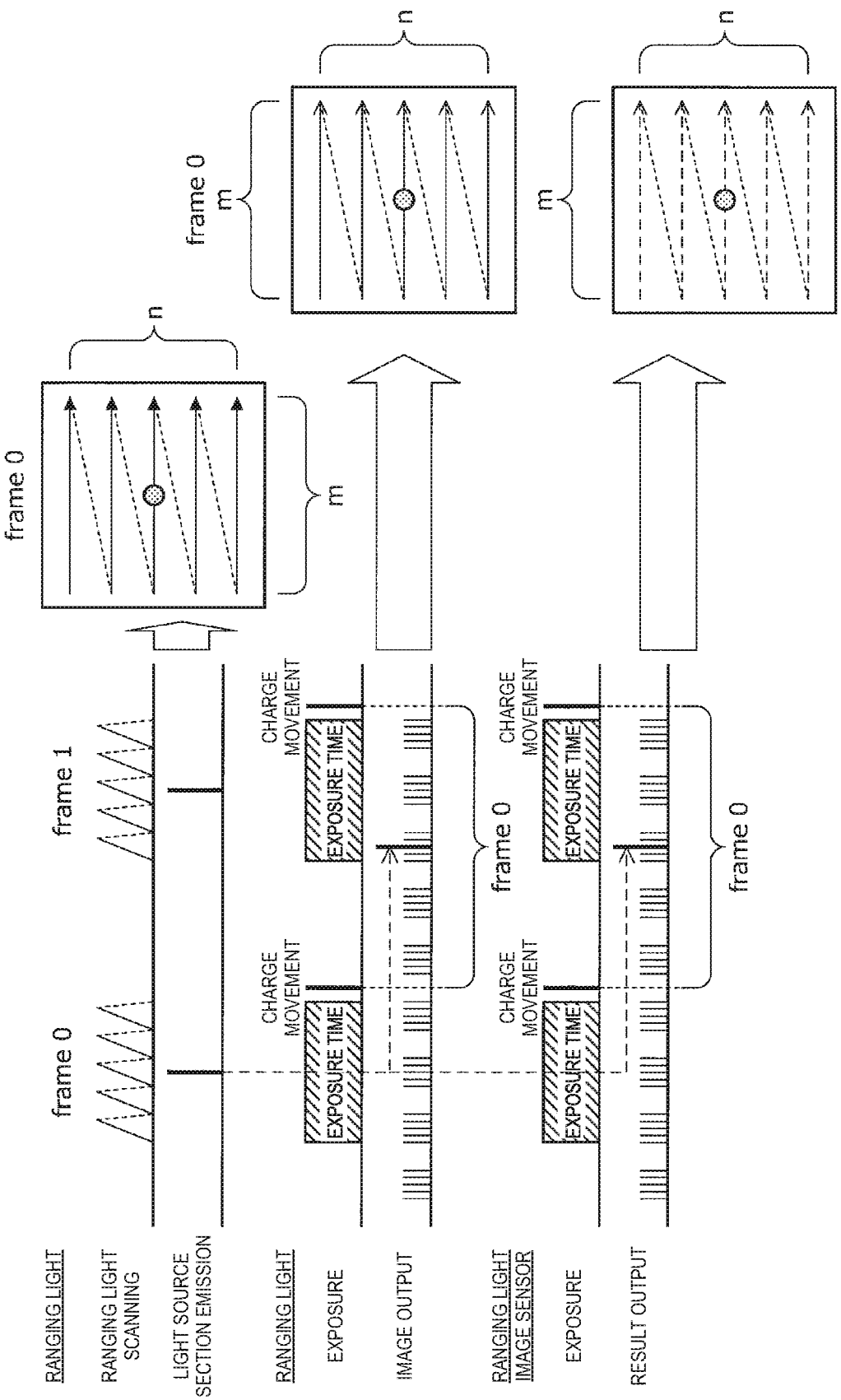
FIG. 6 is an explanatory diagram for describing control processing in the imaging device according to the embodiment.

The ranging control section 163 and the imaging control section 165 according to the present embodiment cooperate with each other and exert control such that the scan timing of the scanning mirror SM of the applied position control section 111, the exposure time of the ranging light image sensor 103, and the exposure time of the image sensor 105 synchronize with one another, as in a timing chart shown on the left side of FIG. 6.

Here, when ranging light is output from the ranging light source section 101 at the time when the scanning mirror SM reaches a user designated position, such an output timing is set to be located within the exposure time in the ranging light image sensor 103 and the image sensor 105. Thus, the ranging light output from the ranging light source section 101 is imaged at the same position in the ranging light image sensor 103 and the image sensor 105 at the same timing, as schematically shown on the right side of FIG. 6.

Figure 7:
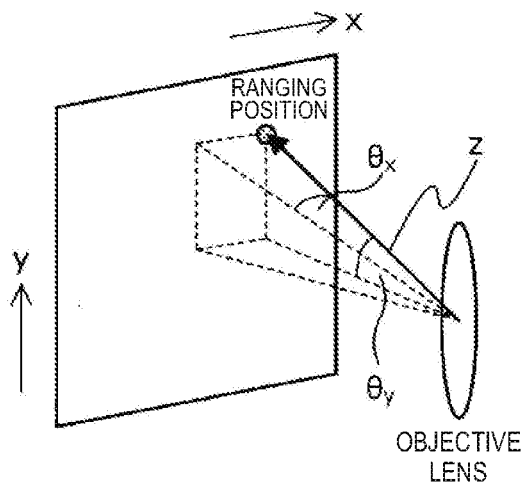
FIG. 7 is an explanatory diagram for describing control processing in the imaging device according to the embodiment.

Here, the distance information calculating section 167 calculates the spaced distance on the basis of a detection signal of the ranging light image sensor 103 acquired from the ranging control section 163. Now, as shown in FIG. 7, it is assumed that an objective lens having a conjugate relation with the ranging light image sensor 103 exists, and the spaced distance between such an objective lens and the ranging position on the imaging target S is expressed as z. In this case, the distance information calculating section 167 first calculates the spaced distance z in FIG. 7 on the basis of the TOF method.

In addition, the distance information calculating section 167 can acquire, from the ranging control section 163, angular information $(\theta_x, \theta_y)$ of the scanning mirror SM in the applied position control section 111 when the ranging light is output. Assuming that relative position coordinates of the ranging position is expressed as (x, y), the relations of Expression 101a and Expression 101b below hold, as is clear from the geometric positional relation shown in FIG. 7.

$x=z\times\cos(\theta_x)$ (Expression 101a)

$y=z\times\cos(\theta_y)$ (Expression 101b)

Therefore, the distance information calculating section 167 can further calculate the position coordinates (x, y) of the ranging position utilizing the acquired angular information $(\theta_x, \theta_y)$ of the scanning mirror SM and the calculated spaced distance z.

Figure 8:
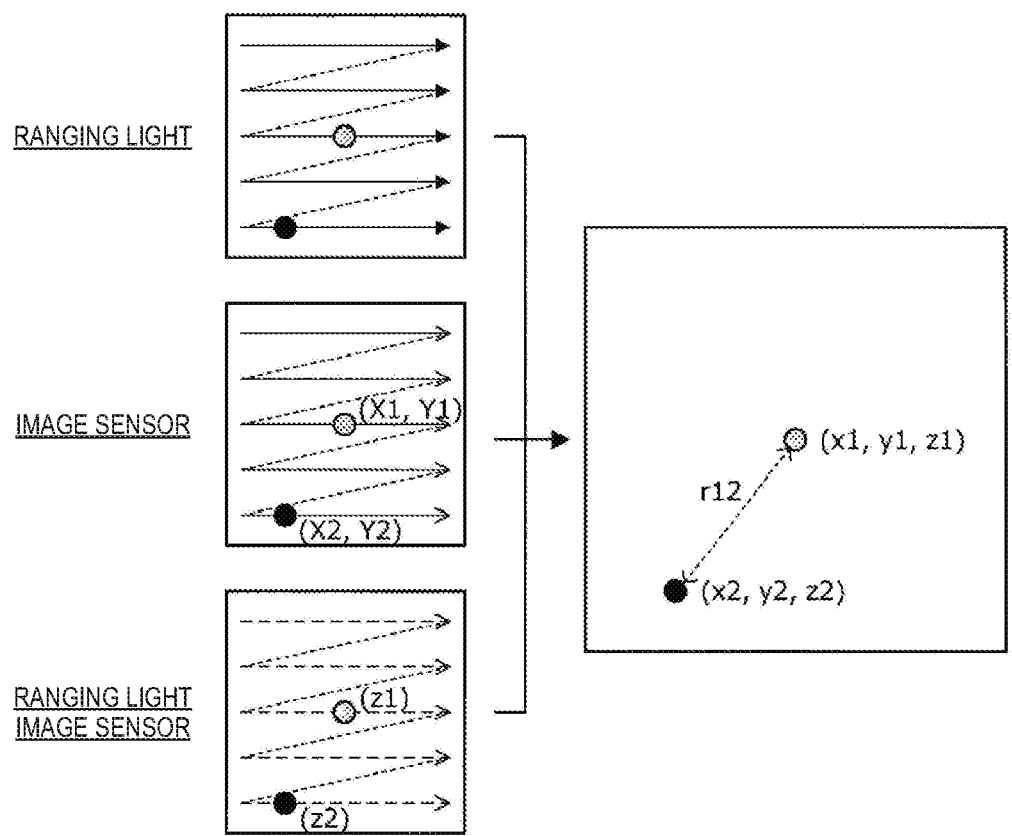
FIG. 8 is an explanatory diagram for describing control processing in the imaging device according to the embodiment.

Here, as shown in FIG. 8, it is assumed that the ranging light is output at two positions during a certain exposure time. In this case, the distance information calculating section 167 can calculate spaced distances z1 and z2 to the two ranging positions, respectively, in line with the above-described method. Thereafter, the distance information calculating section 167 can calculate respective position coordinates (x1, y1) and (z2, y2) utilizing angular information of the scanning mirror SM at the respective ranging positions. Accordingly, the distance information calculating section 167 can specify coordinates (x, 1, y1, z1) and (x2, y2, z2) of the two ranging positions. In addition, in the case where two or more ranging positions exist, the distance information calculating section 167 is capable of further calculating relative distance information (that is, a distance r12 between the two points) as distance information utilizing the calculated spatial coordinates of the respective ranging positions.

Figure 9:
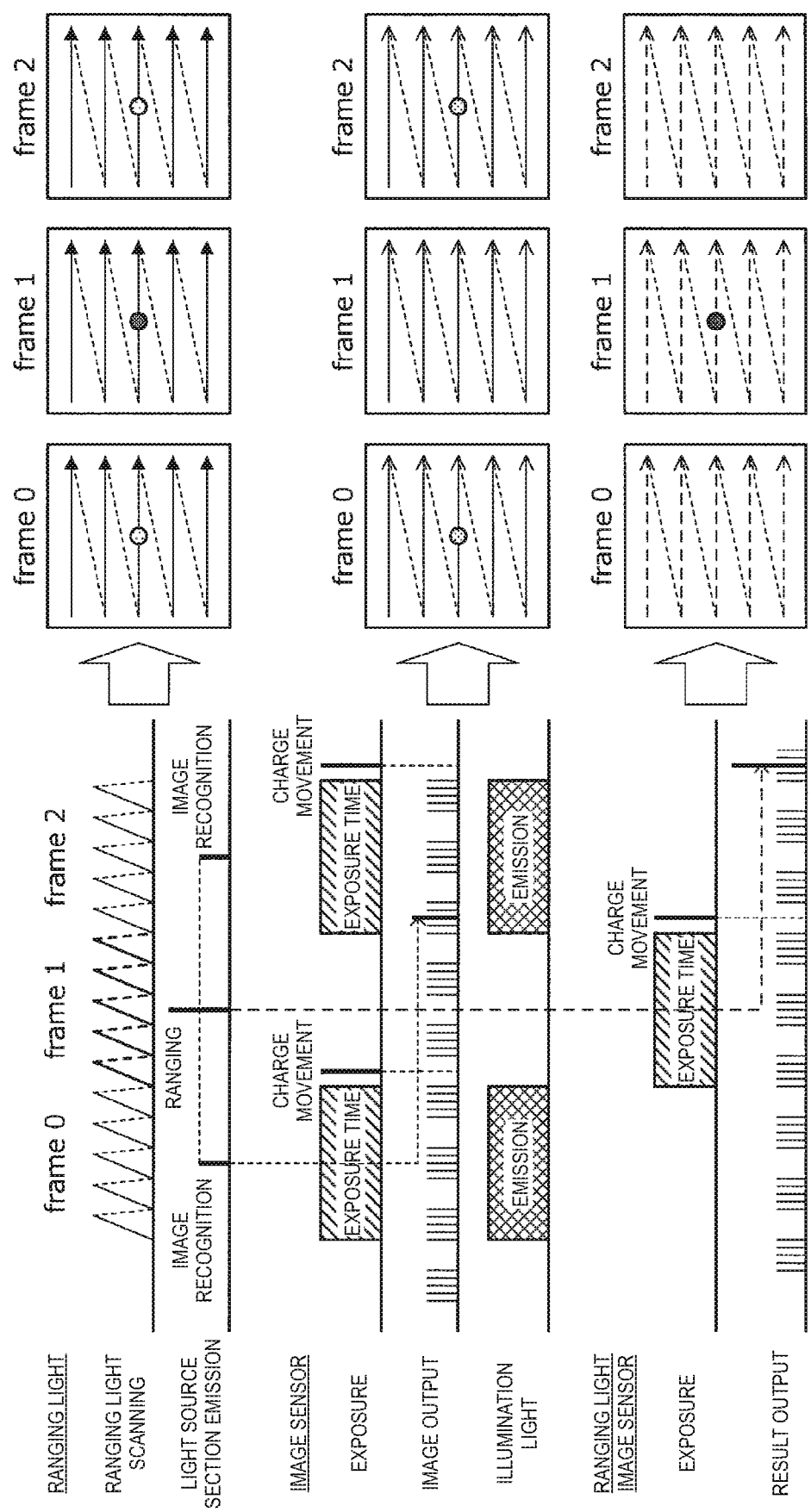
FIG. 9 is an explanatory diagram for describing control processing in the imaging device according to the embodiment.

In addition, as shown in FIG. 9, the ranging control section 163 and the imaging control section 165 may exert control such that ranging light is emitted at a relatively low intensity (for example, an intensity less than a predetermined threshold value) during the exposure time of the image sensor 105, while ranging light is emitted at a relatively high intensity (for example, an intensity more than or equal to the predetermined threshold value) at the time of ranging.

In such a case, the ranging cycle becomes twice the ranging cycle in the case shown in FIG. 6 as is also clear from FIG. 9, however, it is possible to prevent the output of the image sensor 105 from being saturated due to the ranging light leaked into the image sensor 105.

On this occasion, it is preferable that the imaging control section 165 turns off the light source of illumination light to be used for generating an observed image of the imaging target S during the exposure time of the ranging light image sensor 103 to prevent leakage of the illumination light into the ranging light image sensor 103, as shown in FIG. 9. Accordingly, it is possible to further improve the ranging accuracy in the imaging device 10 according to the present embodiment.

Figure 10:
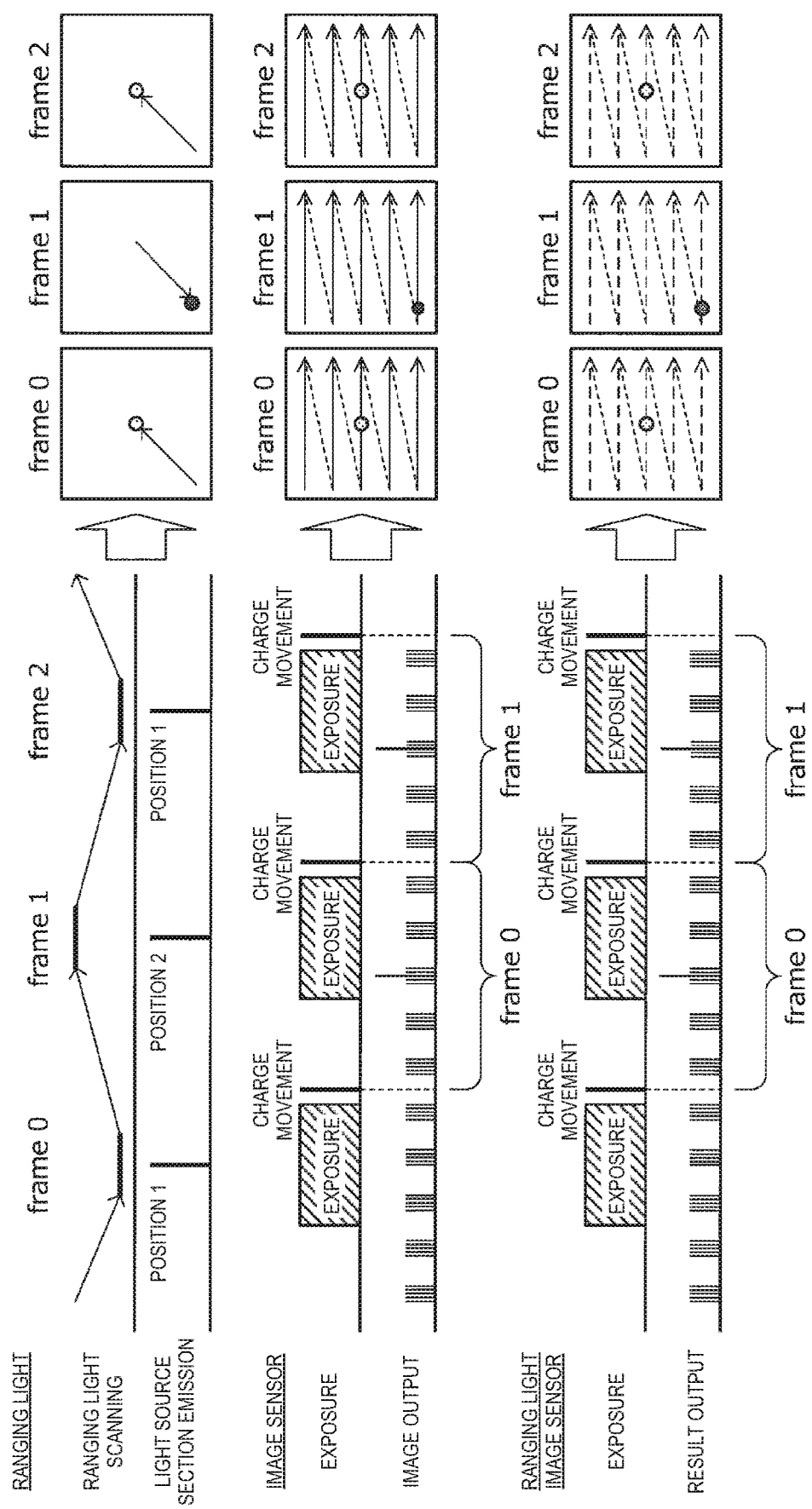
FIG. 10 is an explanatory diagram for describing control processing in the imaging device according to the embodiment.
Figure 11:
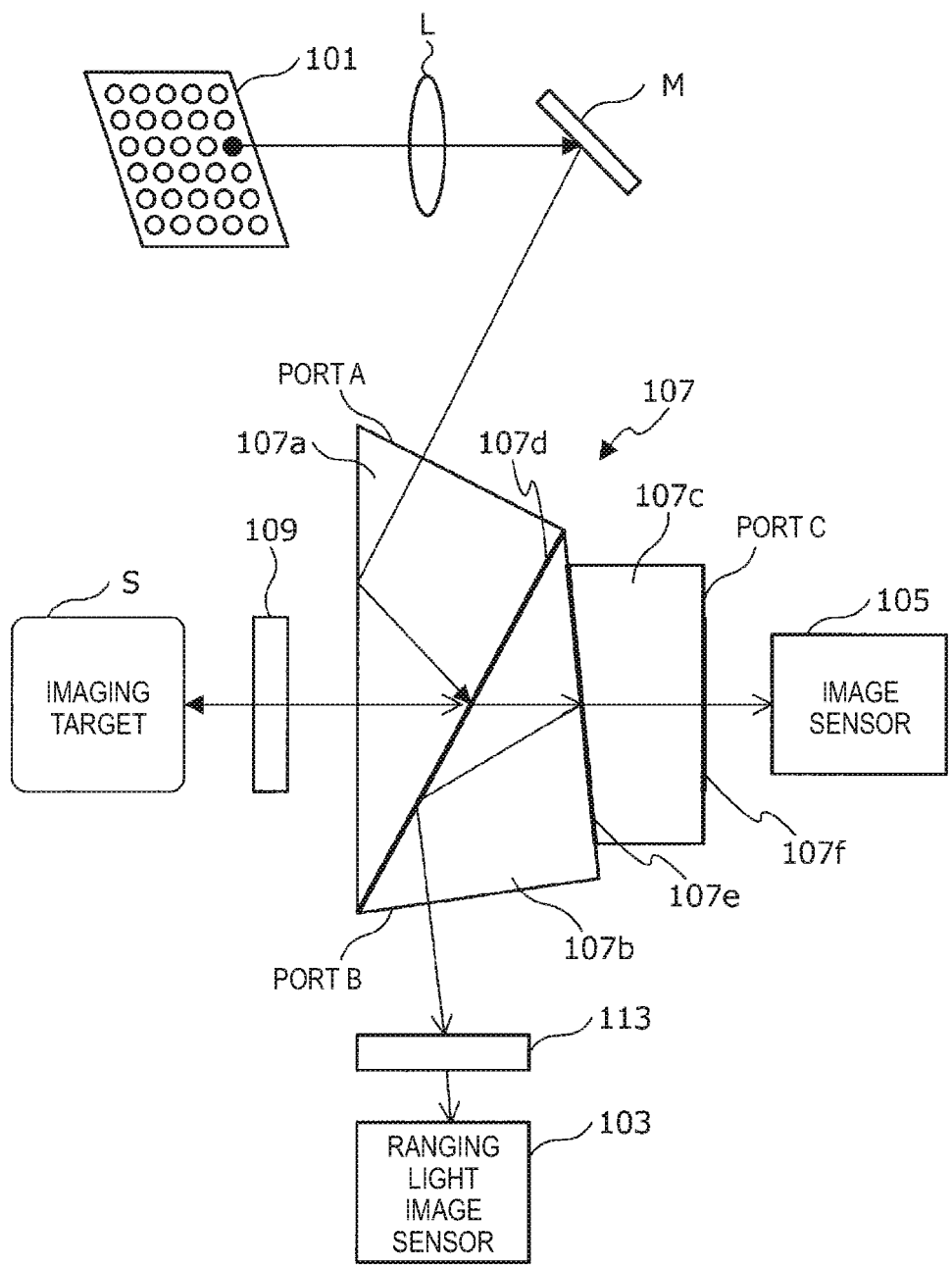
FIG. 11 is an explanatory diagram schematically showing an example of a configuration of the imaging device according to the embodiment.

In addition, the ranging control section 163 is also capable of causing only a desired position to be partially scanned as shown in FIG. 10, rather than causing the scanning mirror SM to perform scanning regularly as shown in FIG. 6 and FIG. 9. Accordingly, it is possible to carry out ranging processing at each position designated by the user more easily.

The control processing of the imaging optical system carried out in the control section 151 according to the present embodiment has been described above in detail with reference to FIG. 6 to FIG. 10 while providing examples.

The above thus illustrates an example of the functions of the arithmetic processing section 150 according to the present embodiment. Each of the above structural elements may be realized using general-purpose members or circuits, but may also be realized in hardware specialized in the function of each structural element. Additionally, the functions of each of the structural elements may also be conducted entirely by a CPU or the like. Consequently, it is possible to appropriately modify the configuration to be used according to the technological level at the time of carrying out the present embodiment.

Note that it is also possible to develop a computer program for realizing the respective functions of an arithmetic processing section according to the present embodiment as discussed above, and implement the computer program in a personal computer or the like. In addition, a computer-readable recording medium storing such a computer program may also be provided. The recording medium may be a magnetic disk, an optical disc, a magneto-optical disk, or flash memory, for example. Furthermore, the above computer program may also be delivered via a network, for example, without using a recording medium.

[With Regard to Variation of Ranging Light Source Section 101]

In the example described above, the case in which ranging light output from the ranging light source section 101 is a point light source, and the applied position of ranging light is controlled by the scanning mirror MS of the applied position control section 111 as shown in FIG. 3A and FIG. 3B has been described. However, as schematically shown in FIG. 11, by adopting an array light source in which emission points from which the ranging light can be output are arranged in an array as the ranging light source section 101, it is possible to control the applied position of ranging light merely by guiding the ranging light using the typical lens L and a mirror M, without providing the applied position control section 111 (in more detail, the scanning mirror MS). In this case, as schematically shown in FIG. 11, when an emission point in the array light source is selected, the applied position of the ranging light on the imaging target is controlled. As a result, it is possible to further reduce the imaging device 10 in size.

Note that, in the case of using the array light source as shown in FIG. 11 as the ranging light source section 101, it is preferable to maximize the number of emission points in the array light source. Accordingly, it is possible to control the applied position of ranging light more finely, and to improve the ranging resolution.

The imaging device 10 according to the present embodiment has been described above in detail with reference to FIG. 2 to FIG. 11.

<With Regard to Endoscope>

Figure 12:
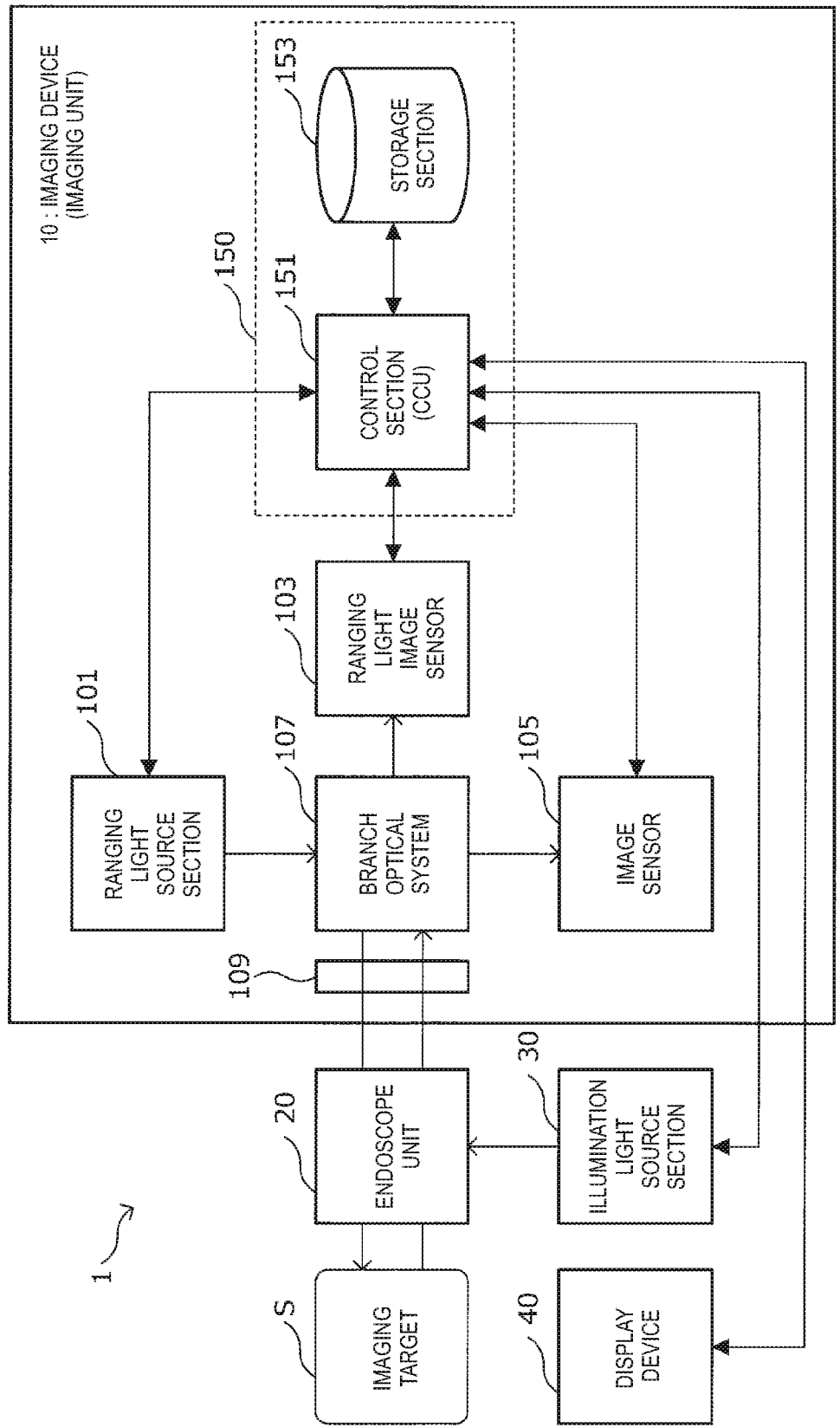
FIG. 12 is an explanatory diagram schematically showing an example of a configuration of an endoscope having the imaging device according to the embodiment.

Next, a configuration of an endoscope 1 including the imaging device 10 according to the present embodiment will be briefly described below with reference to FIG. 12. FIG. 12 is an explanatory diagram schematically showing an example of a configuration of the endoscope having the imaging device according to the present embodiment.

It is possible to utilize the imaging device 10 according to the present embodiment as described above as an imaging unit in various endoscopes such as a general medical endoscope and joint mirror, an industrial endoscope, and the like.

The endoscope 1 according to the present embodiment has the imaging device 10 according to the present embodiment, an endoscope unit 20, and an illumination light source section 30, as schematically shown in FIG. 12. In addition, it is preferable that the endoscope 1 according to the present embodiment further has a display device 40, as schematically shown in FIG. 12.

The imaging device 10 according to the present embodiment as described above is optically connected to the endoscope unit 20 as an imaging unit in an endoscope system. Here, the endoscope unit 20 to which the imaging device 10 according to the present embodiment is connected is not particularly limited, but it is possible to utilize publicly-known various endoscopes.

On this occasion, the arithmetic processing section 150 (in more detail, the control section 151) that the imaging device 10 according to the present embodiment has functions as a camera control unit (CCU) in a general endoscope system. Accordingly, the control section 151 of the arithmetic processing section 150 is capable of controlling the endoscope unit 20, the illumination light source section 30, and the display device 40 in the endoscope 1 to be brought into a desired state.

The illumination light source section 30 outputs illumination light such as white light, for example, to light guide fibers of the endoscope unit 20 at a predetermined timing under the control of the arithmetic processing section 150 (in more detail, the control section 151) according to the present embodiment. Accordingly, the surface of the imaging target S is illuminated uniformly with illumination light output from the illumination light source section 30, and the imaging device 10 is capable of capturing an observed image of the imaging target S. Such an illumination light source section 30 is not particularly limited, but it is possible to use a general illumination light source for use in an endoscope system.

The display device 40 is an output device such as a display provided for the endoscope 1, and an observed image of the imaging target S captured by the imaging device 10 and various types of distance information concerning the imaging target are displayed. This allows a user of the endoscope 1 according to the present embodiment to grasp in situ an observed image of the imaging target S captured by the imaging device 10 and various types of distance information concerning the imaging target, and to conduct more appropriate medical actions and the like.

Note that the case in which the arithmetic processing section 150 of the imaging device 10 according to the present embodiment functions as a CCU has been described in the example shown in FIG. 12, whilst the endoscope 1 according to the present embodiment is not limited to such a case, but a CCU may exist in addition to the arithmetic processing section 150. In this case, the arithmetic processing section 150 according to the present embodiment carries out the imaging processing and ranging processing as described above while cooperating with an existing CCU.

The configuration of the endoscope 1 including the imaging device 10 according to the present embodiment has been briefly described above with reference to FIG. 12.

As described above, since incident light and optical feedback of ranging light become coaxial optical paths in the imaging device 10 according to the present embodiment, it is possible to suppress detection errors in the TOF method extremely. In addition, since it is possible to guide ranging light only to a desired ranging position, it is possible to suppress light source power of the ranging light source section 101, which can improve the light utilization efficiency.

In addition, since it is possible to achieve size reduction because of improvement in ranging accuracy, low power consumption, and the like in the case of utilizing the imaging device 10 according to the present embodiment as an imaging unit in an endoscope, correct determinations and treatments by doctors can be made without increasing burdens on the doctors.

<With Regard to Hardware Configuration>

Figure 13:
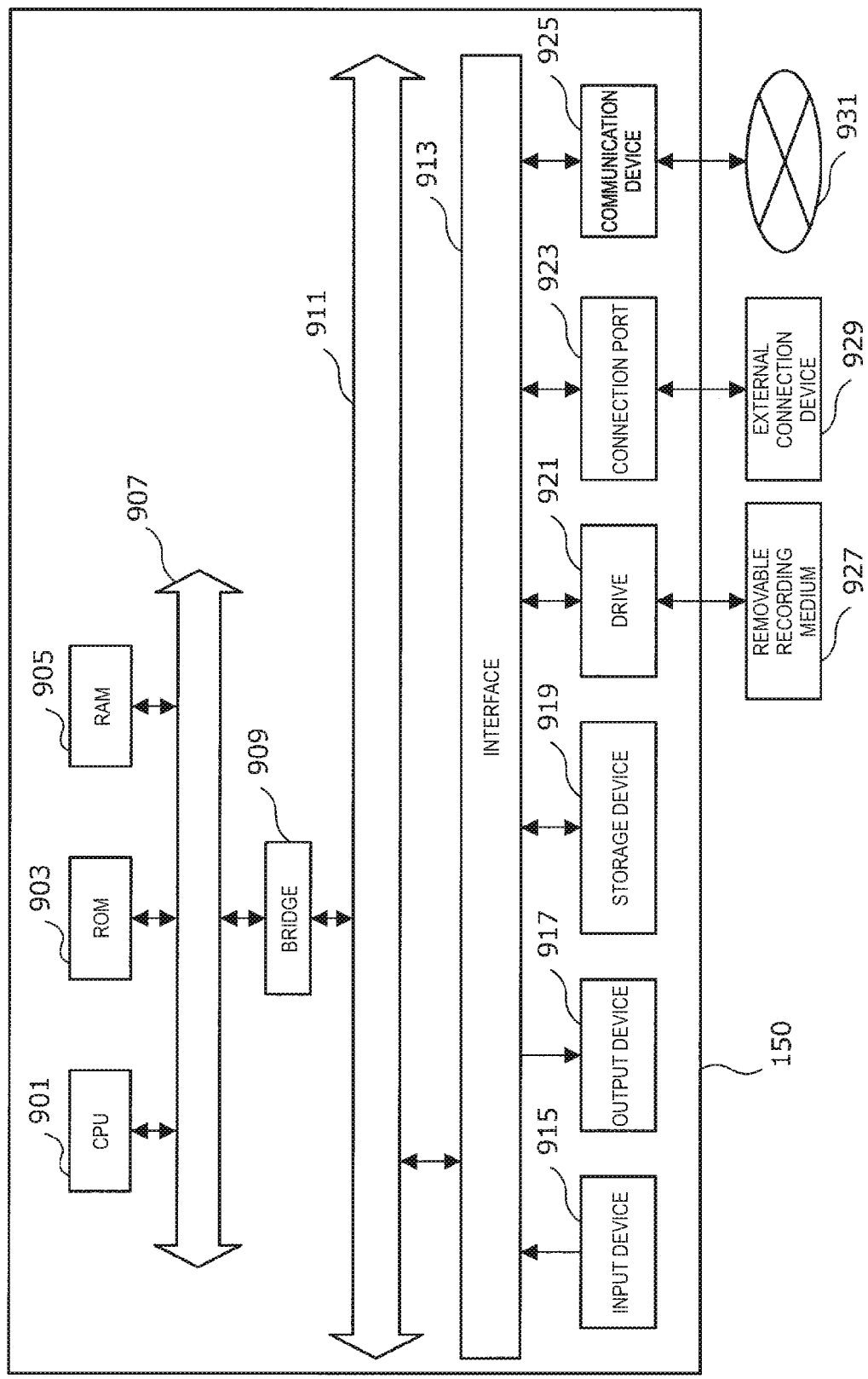
FIG. 13 is a block diagram showing an example of a hardware configuration of a control section according to an embodiment of the present disclosure.

Next, the hardware configuration of the arithmetic processing section 150 according to the embodiment of the present disclosure is described in detail with reference to FIG. 13. FIG. 13 is a block diagram for illustrating the hardware configuration of the arithmetic processing section 150 according to the embodiment of the present disclosure.

The arithmetic processing section 150 mainly include a CPU 901, a ROM 903, and a RAM 905. Furthermore, the arithmetic processing section 150 also includes a host bus 907, a bridge 909, an external bus 911, an interface 913, an input device 915, an output device 917, a storage device 919, a drive 921, a connection port 923, and a communication device 925.

The CPU 901 serves as an arithmetic processing apparatus and a control apparatus, and controls the overall operation or a part of the operation of the arithmetic processing section 150 according to various programs recorded in the ROM 903, the RAM 905, the storage device 919, or a removable recording medium 927. The ROM 903 stores programs, operation parameters, and the like used by the CPU 901. The RAM 905 primarily stores programs by the CPU 901 and parameters and the like varying as appropriate during the execution of the programs. These are connected with each other via the host bus 907 including an internal bus such as a CPU bus.

The host bus 907 is connected to the external bus 911 such as a peripheral component interconnect/interface (PCI) bus via the bridge 909.

The input device 915 is operation means operated by a user, such as a mouse, a keyboard, a touch panel, buttons, a switch and a lever. Also, the input device 915 may be remote control means (a so-called remote control) using, for example, infrared light or other radio waves, or may be an external connection device 929 such as a mobile phone or a PDA conforming to the operation of the arithmetic processing section 150. Furthermore, the input device 915 generates an input signal on the basis of, for example, information which is inputted by a user with the above operation means, and includes an input control circuit or the like for outputting the input signal to the CPU 901. The user of the arithmetic processing section 150 can input various data to the arithmetic processing section 150 and can instruct the arithmetic processing section 150 to perform processing by operating the input apparatus 915.

The output device 917 is includes a device capable of visually or audibly notifying acquired information to a user. Examples of such a device include display devices such as a CRT display device, a liquid crystal display device, a plasma display device, an EL display device and lamps, audio output devices such as a speaker and a headphone, a printer, a mobile phone, a facsimile machine, and the like. For example, the output device 917 outputs a result obtained by various processing performed by the arithmetic processing section 150. More specifically, the display device displays, in the form of texts or images, a result obtained by various processes performed by the arithmetic processing section 150. On the other hand, the audio output device converts an audio signal such as reproduced audio data and sound data into an analog signal, and outputs the analog signal.

The storage device 919 is a device for storing data included as an example of a storage unit of the arithmetic processing section 150 and is used to store data. The storage device 919 includes, for example, a magnetic storage device such as a hard disk drive (HDD), a semiconductor storage device, an optical storage device, or a magneto-optical storage device. The storage device 919 stores programs to be executed by the CPU 901, and externally obtained various data or the like.

The drive 921 is a reader/writer for a recording medium, and is embedded in the arithmetic processing section 150 or attached externally thereto. The drive 921 reads information recorded in the attached removable recording medium 927 such as a magnetic disk, an optical disc, a magneto-optical disk, or a semiconductor memory, and outputs the read information to the RAM 905. Furthermore, the drive 921 can write a record in the attached removable recording medium 927 such as a magnetic disk, an optical disc, a magneto-optical disk, or a semiconductor memory. The removable recording medium 927 is, for example, a DVD medium, an HD-DVD medium, or a Blu-ray (registered trademark) medium. The removable recording medium 927 may be a CompactFlash (CF, registered trademark), a flash memory, a secure digital (SD) memory card, or the like. Alternatively, the removable recording medium 927 may be, for example, an integrated circuit (IC) card equipped with a non-contact IC chip, an electronic appliance, or the like.

The connection port 923 is a port for allowing devices to directly connect to the arithmetic processing section 150. Examples of the connection port 923 include a universal serial bus (USB) port, an IEEE1394 port, a small computer system interface (SCSI) port, and the like. Other examples of the connection port 923 include an RS-232C port, an optical audio terminal, a high-definition multimedia interface (HDMI, registered trademark) port, and the like. By connecting the external connection device 929 to the connection port 923, the arithmetic processing section 150 directly acquires various data from the external connection device 929 and provides various data to the external connection device 929.

The communication device 925 is a communication interface including, for example, a communication device for establishing a connection to a communication network 931. The communication device 925 is, for example, a wired or wireless local area network (LAN), Bluetooth (registered trademark), a communication card for a wireless USB (WUSB), or the like. Alternatively, the communication device 925 may be a router for optical communication, a router for an asymmetric digital subscriber line (ADSL), a modem for various communications, or the like. The communication device 925 can transmit and receive signals and the like in accordance with a predetermined protocol such as TCP/IP or the like on the Internet and with other communication devices, for example. Further, the communication network 931 connected to the communication device 925 includes a network and the like, which is connected via wire or wirelessly, and may be, for example, the Internet, a home LAN, infrared communication, radio wave communication, satellite communication, or the like.

Heretofore, an example of the hardware configuration capable of realizing the functions of the arithmetic processing section 150 according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An imaging device including:

a ranging light source section configured to output ranging light for measuring a distance to an imaging target at a predetermined timing;

an image sensor on which an image of the imaging target is formed;

a ranging light image sensor on which optical feedback of the ranging light from the imaging target is imaged;

a branch optical system configured to coaxially branch incident light into three types of optical paths different from one another; and a distance information calculating section configured to calculate distance information concerning the imaging target on a basis of a result of detection of the optical feedback obtained by the ranging light image sensor, in which in the branch optical system, a first optical path among the three types of optical paths is used as an optical path configured to guide the ranging light whose applied position on the imaging target has been controlled to the imaging target, a second optical path among the three types of optical paths is used as an optical path configured to form an image of the imaging target on the image sensor, and a third optical path among the three types of optical paths is used as an optical path configured to image the optical feedback on the ranging light image sensor, and the distance information calculating section calculates a spaced distance to the imaging target by a Time Of Flight method on the basis of the result of detection of the optical feedback.

(2)

The imaging device according to (1), in which the distance information calculating section further calculates position coordinates of a ranging position on a basis of information concerning the applied position of the ranging light and the spaced distance as calculated.

(3)

The imaging device according to (1) or (2), in which in a case where the optical feedback is detected at a plurality of positions during an exposure time of the ranging light image sensor, the distance information calculating section calculates position coordinates of a ranging position for each of the positions at which the optical feedback has been detected, and calculates a relative distance between the respective ranging positions.

(4)

The imaging device according to any one of (1) to (3), in which the ranging light source section outputs light belonging to a visible light wavelength band or a near-infrared wavelength band as the ranging light, the image sensor and the ranging light image sensor are installed such that pixel arrangements correspond to each other, and the second optical path is set such that a part of the optical feedback is imaged on the image sensor configured to image light of the visible light wavelength band, and the part of the optical feedback imaged on the image sensor is used as a guide indicating a ranging position.

(5)

The imaging device according to any one of (1) to (4), in which the ranging light is controlled such that an output intensity becomes less than a predetermined threshold value during an exposure time of the image sensor, and controlled such that the output intensity becomes more than or equal to the predetermined threshold value during an exposure time of the ranging light image sensor.

(6)

The imaging device according to any one of (1) to (5), in which the branch optical system is a spectrum prism having three types of optical prisms bonded to one another, and the three types of optical paths are generated when a bonding surface between the optical prisms adjacent to each other functions as at least any of a beam splitter, a polarizing beam splitter, or a wavelength selection filter.

(7)

The imaging device according to any one of (1) to (5), in which the branch optical system includes a polarizing beam splitter and a beam splitter.

(8)

The imaging device according to any one of (1) to (7), further including:

an applied position control section configured to control an applied position of the ranging light of a point light source output from the ranging light source section on the imaging target, in which the applied position control section controls the applied position of the ranging light on the imaging target by scanning the applied position of the ranging light of the point light source.

(9)

The imaging device according to any one of (1) to (7), in which in the ranging light source section, emission points from which the ranging light can be output are arranged in an array, and an applied position of the ranging light on the imaging target is controlled by making a selection from among the array emission points.

(10)

The imaging device according to any one of (1) to (9), in which a bandpass filter in which a wavelength of the ranging light serves as a central wavelength is provided between the branch optical system and the ranging light image sensor.

(11)

The imaging device according to any one of (1) to (10), in which illumination light for capturing an image of the imaging target is turned off during an exposure time of the ranging light image sensor.

(12)

The imaging device according to any one of (1) to (11), in which the branch optical system is optically connected to an endoscope unit, and an image of the imaging target is captured through the endoscope unit.

(13)

An endoscope including:

an imaging device including a ranging light source section configured to output ranging light for measuring a distance to an imaging target at a predetermined timing, an image sensor on which an image of the imaging target is formed, a ranging light image sensor on which optical feedback of the ranging light from the imaging target is imaged,
a branch optical system configured to coaxially branch incident light into three types of optical paths different from one another, and
a distance information calculating section configured to calculate distance information concerning the imaging target on a basis of a result of detection of the optical feedback obtained by the ranging light image sensor, in which
in the branch optical system, a first optical path among the three types of optical paths is used as an optical path configured to guide the ranging light whose applied position on the imaging target has been controlled to the imaging target, a second optical path among the three types of optical paths is used as an optical path configured to form an image of the imaging target on the image sensor, and a third optical path among the three types of optical paths is used as an optical path configured to image the optical feedback on the ranging light image sensor, and
the distance information calculating section calculates a spaced distance to the imaging target by a Time Of Flight method on the basis of the result of detection of the optical feedback;
an endoscope unit optically connected to the branch optical system; and
an illumination light source section configured to output illumination light for obtaining an image of the imaging target.

REFERENCE SIGNS LIST 1 endoscope
10 imaging device (imaging unit)
20 endoscope unit
30 illumination light source section
40 display device
101 ranging light source section
103 ranging light image sensor
105 image sensor
107 branch optical system
109 quarter wave plate
111 applied position control section
113 bandpass filter
150 arithmetic processing section
151 control section
153 storage section
161 integral control section
163 ranging control section
165 imaging control section
167 distance information calculating section
169 image processing section
171 processing result output section
173 display control section

The invention claimed is:

1. An imaging device comprising:
a ranging light source configured to output ranging light for measuring a distance to an imaging target at a predetermined timing;
an image sensor on which an image of the imaging target is formed;
a ranging light image sensor on which optical feedback of the ranging light from the imaging target is imaged;
a branch optical system configured to coaxially branch incident light into three types of optical paths different from one another; and
a distance information calculating circuitry configured to calculate distance information concerning the imaging target on a basis of a result of detection of the optical feedback obtained by the ranging light image sensor, wherein
in the branch optical system, a first optical path among the three types of optical paths is used as an optical path configured to guide the ranging light whose applied position on the imaging target has been controlled to the imaging target, a second optical path among the three types of optical paths is used as an optical path configured to form an image of the imaging target on the image sensor, and a third optical path among the three types of optical paths is used as an optical path configured to image the optical feedback on the ranging light image sensor,
illumination light for illuminating the imaging target does not travel the first optical path, and
the distance information calculating circuitry is configured to calculate a spaced distance to the imaging target by a Time Of Flight method on the basis of the result of detection of the optical feedback.

2. The imaging device according to claim 1, wherein the distance information calculating circuitry is further configured to calculate position coordinates of a ranging position on a basis of information concerning the applied position of the ranging light and the spaced distance as calculated.

3. The imaging device according to claim 1, wherein in a case where the optical feedback is detected at a plurality of positions during an exposure time of the ranging light image sensor, the distance information calculating circuitry is further configured to calculate position coordinates of a ranging position for each of the positions at which the optical feedback has been detected, and a relative distance between the respective ranging positions.

4. The imaging device according to claim 1, wherein the ranging light source outputs light belonging to a visible light wavelength band or a near-infrared wavelength band as the ranging light,
the image sensor and the ranging light image sensor are installed such that pixel arrangements correspond to each other, and
the second optical path is set such that a part of the optical feedback is imaged on the image sensor configured to image light of the visible light wavelength band, and the part of the optical feedback imaged on the image sensor is used as a guide indicating a ranging position.

5. The imaging device according to claim 1, wherein the ranging light is controlled such that an output intensity becomes less than a predetermined threshold value during an exposure time of the image sensor, and controlled such that the output intensity becomes more than or equal to the predetermined threshold value during an exposure time of the ranging light image sensor.

6. The imaging device according to claim 1, wherein the branch optical system is a spectrum prism having three types of optical prisms bonded to one another, and
the three types of optical paths are generated when a bonding surface between the optical prisms adjacent to each other functions as at least any of a beam splitter, a polarizing beam splitter, or a wavelength selection filter.

7. The imaging device according to claim 1, wherein the branch optical system includes a polarizing beam splitter and a beam splitter.

8. The imaging device according to claim 1, further comprising:
an applied position control circuitry configured to control an applied position of the ranging light of a point light source output from the ranging light source on the imaging target, wherein
the applied position control circuitry is configured to control the applied position of the ranging light on the imaging target by scanning the applied position of the ranging light of the point light source.

9. The imaging device according to claim 1, wherein
in the ranging light source, emission points from which the ranging light can be output are arranged in an array, and
an applied position of the ranging light on the imaging target is controlled by making a selection from among the array emission points.

10. The imaging device according to claim 1, wherein
a bandpass filter in which a wavelength of the ranging light serves as a central wavelength is provided between the branch optical system and the ranging light image sensor.

11. The imaging device according to claim 1, wherein
illumination light for capturing an image of the imaging target is turned off during an exposure time of the ranging light image sensor.

12. The imaging device according to claim 1, wherein
the branch optical system is optically connected to an endoscope unit, and
an image of the imaging target is captured through the endoscope unit.

13. An endoscope comprising:
an imaging device including
a ranging light source configured to output ranging light for measuring a distance to an imaging target at a predetermined timing,
an image sensor on which an image of the imaging target is formed,
a ranging light image sensor on which optical feedback of the ranging light from the imaging target is imaged,
a branch optical system configured to coaxially branch incident light into three types of optical paths different from one another, and
a distance information calculating circuitry configured to calculate distance information concerning the imaging target on a basis of a result of detection of the optical feedback obtained by the ranging light image sensor,
wherein
in the branch optical system, a first optical path among the three types of optical paths is used as an optical path configured to guide the ranging light whose applied position on the imaging target has been controlled to the imaging target, a second optical path among the three types of optical paths is used as an optical path configured to form an image of the imaging target on the image sensor, and a third optical path among the three types of optical paths is used as an optical path configured to image the optical feedback on the ranging light image sensor, and the distance information calculating section calculates a spaced distance to the imaging target by a Time Of Flight method on the basis of the result of detection of the optical feedback;
an endoscope unit optically connected to the branch optical system; and
an illumination light source configured to output illumination light for obtaining an image of the imaging target, wherein the illumination light source is separate from the imagine device.

14. The endoscope according to claim 13, wherein
the ranging light source outputs light belonging to a visible light wavelength band or a near-infrared wavelength band as the ranging light,
the image sensor and the ranging light image sensor have pixel arrangements correspond to each other, and
the second optical path is set such that a part of the optical feedback is imaged on the image sensor configured to image light of the visible light wavelength band, and the part of the optical feedback imaged on the image sensor is used as a guide indicating a ranging position.

15. The endoscope according to claim 13, wherein
the ranging light is controlled such that an output intensity becomes less than a predetermined threshold value during an exposure time of the image sensor, and controlled such that the output intensity becomes more than or equal to the predetermined threshold value during an exposure time of the ranging light image sensor.

16. The endoscope according to claim 13, further comprising control circuitry configured to control the ranging light source such that
an output intensity becomes less than a predetermined threshold value during an exposure time of the image sensor with the illumination light, and
the output intensity becomes more than or equal to the predetermined threshold value during an exposure time of the ranging light image sensor.

17. The imaging device according to claim 1, further comprising control circuitry configured to control the ranging light source such that
an output intensity is less than a predetermined threshold value during an exposure time of the image sensor with the illumination light, and
the output intensity is more than or equal to the predetermined threshold value during an exposure time of the ranging light image sensor.

18. An imaging method, comprising:
outputting ranging light for measuring a distance to an imaging target at a predetermined timing along a first optical path configured to guide the ranging light whose applied position on the imaging target has been controlled to the imaging target;
receiving light along a second optical path configured to form an image of the imaging target illuminated by illumination light on an image sensor;
receiving ranging light along a third optical path configured to image optical feedback on a ranging light image sensor, the first to third optical paths being three different optical paths, wherein the illumination light for illuminating the imaging target does not travel the first optical path; and
calculating distance information concerning the imaging target on a basis of a result of detection of the optical feedback obtained by the ranging light image sensor, including calculating a spaced distance to the imaging target by a Time Of Flight method on the basis of the result of detection of the optical feedback.

19. The imaging method according to claim 18, wherein the ranging light is in a visible light wavelength band or a near-infrared wavelength band,
the image sensor and the ranging light image sensor have pixel arrangements correspond to each other, and
further comprising setting the second optical path such that a part of the optical feedback is imaged on the image sensor configured to image light of the visible light wavelength band, and the part of the optical feedback imaged on the image sensor is used as a guide indicating a ranging position.

20. The method according to claim 18, further comprising controlling the ranging light to have an output intensity less than a predetermined threshold value during an exposure time of the image sensor, and more than or equal to the predetermined threshold value during an exposure time of the ranging light image sensor.

* * * * *